United States Patent
Bebbington et al.

(10) Patent No.: US 7,074,782 B2
(45) Date of Patent: *Jul. 11, 2006

(54) CARBAMATE CASPASE INHIBITORS AND USES THEREOF

(75) Inventors: David Bebbington, Pewsey (GB); Ronald Knegtel, Abingdom (GB); Michael Mortimore, Westbridgefored (GB); David Kay, Wiltshire (GB); Julian M. C. Golec, Swindon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/645,043

(22) Filed: Aug. 21, 2003

(65) Prior Publication Data

US 2004/0053920 A1    Mar. 18, 2004

Related U.S. Application Data

(62) Division of application No. 09/821,161, filed on Mar. 29, 2001, now Pat. No. 6,689,784.

(60) Provisional application No. 60/192,826, filed on Mar. 29, 2000.

(51) Int. Cl.
| | |
|---|---|
| *C07D 223/18* | (2006.01) |
| *C07D 279/36* | (2006.01) |
| *C07D 405/00* | (2006.01) |
| *C07D 221/12* | (2006.01) |
| *A61K 31/55* | (2006.01) |

(52) U.S. Cl. ............ 514/217; 514/224.8; 514/254.08; 514/254.09; 514/298; 514/411; 514/415; 540/589; 544/31; 544/375; 546/109; 548/441; 548/491; 548/510

(58) Field of Classification Search ............. 548/441, 548/491, 510; 514/411, 415, 224.8, 298, 514/217, 254.08, 254.09; 544/31, 375; 546/109; 540/589
See application file for complete search history.

(56) References Cited

U.S. PATENT DOCUMENTS

| | | |
|---|---|---|
| 6,136,834 A | 10/2000 | Ohmoto et al. |
| 6,153,591 A | 11/2000 | Cai et al. |
| 6,184,210 B1 | 2/2001 | Keana et al. |
| 6,376,484 B1 | 4/2002 | Ohmoto et al. |
| 6,495,522 B1 | 12/2002 | Wang et al. |

FOREIGN PATENT DOCUMENTS

| | | |
|---|---|---|
| EP | 0618223 A2 | 10/1994 |
| WO | WO 91/15577 | 10/1991 |
| WO | WO 93/05071 | 3/1993 |
| WO | WO 96/30395 | 10/1996 |
| WO | WO 97/24339 | 7/1997 |
| WO | WO 98/11129 | 3/1998 |
| WO | WO 98/16502 | 4/1998 |
| WO | WO 98/16505 | 4/1998 |
| WO | WO 99/18781 | 4/1999 |
| WO | WO 99/47154 | 9/1999 |
| WO | WO 00/23421 | 4/2000 |
| WO | WO 00/55114 | 9/2000 |
| WO | WO 00/61542 | 10/2000 |
| WO | WO 01/16093 | 3/2001 |

*Primary Examiner*—Bruck Kifle
(74) *Attorney, Agent, or Firm*—Michael C. Badia; Lisa A. Dixon; Vertex Pharmaceuticals Incorporated

(57) ABSTRACT

This invention provides caspase inhibitors of formula I:

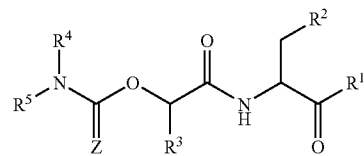

wherein Z is oxygen or sulfur; $R^1$ is hydrogen, $-CHN_2$, R, $CH_2OR$, $CH_2SR$, or $-CH_2Y$; Y is an electronegative leaving group; $R^2$ is $CO_2H$, $CH_2CO_2H$, or esters, amides or isosteres thereof; $R^3$ is a group capable of fitting into the S2 subsite of a caspase enzyme; $R^4$ and $R^5$ are taken together with the intervening nitrogen to form heterocyclic ring and R is as described in the specification. The compounds are effective inhibitors of apoptosis and IL-1β secretion.

45 Claims, No Drawings

CARBAMATE CASPASE INHIBITORS AND USES THEREOF

RELATED APPLICATIONS

This application is a divisional of U.S. patent application Ser. No. 09/821,161, filed Mar. 29, 2001, now U.S. Pat. No. 6,689,784, which claims the benefit of U.S. Provisional Patent Application 60/192,826, filed Mar. 29, 2000, both of which are incorporated in their entirety herein by reference.

FIELD OF THE INVENTION

This invention is in the field of medicinal chemistry and relates to novel compounds, and pharmaceutical compositions thereof, that inhibit caspases that mediate cell apoptosis and inflammation. The invention also relates to methods of using the compounds and pharmaceutical compositions of this invention to treat diseases where caspase activity is implicated.

BACKGROUND OF THE INVENTION

Apoptosis, or programmed cell death, is a principal mechanism by which organisms eliminate unwanted cells. The deregulation of apoptosis, either excessive apoptosis or the failure to undergo it, has been implicated in a number of diseases such as cancer, acute inflammatory and autoimmune disorders, ischemic diseases and certain neurodegenerative disorders (see generally *Science*, 1998, 281, 1283–1312; Ellis et al., *Ann. Rev. Cell. Biol.*, 1991, 7, 663).

Caspases are a family of cysteine protease enzymes that are key mediators in the signaling pathways for apoptosis and cell disassembly (Thornberry, *Chem. Biol.*, 1998, 5, R97–R103). These signaling pathways vary depending on cell type and stimulus, but all apoptosis pathways appear to converge at a common effector pathway leading to proteolysis of key proteins. Caspases are involved in both the effector phase of the signaling pathway and further upstream at its initiation. The upstream caspases involved in initiation events become activated and in turn activate other caspases that are involved in the later phases of apoptosis.

Caspase-1, the first identified caspase, is also known as interleukin converting enzyme or "ICE." Caspase-1 converts precursor interleukin-1β ("pIL-1β") to the pro-inflammatory active form by specific cleavage of pIL-1β between Asp-116 and Ala-117. Besides caspase-1 there are also eleven other known human caspases, all of which cleave specifically at aspartyl residues. They are also observed to have stringent requirements for at least four amino acid residues on the N-terminal side of the cleavage site.

The caspases have been classified into three groups depending on the amino acid sequence that is preferred or primarily recognized. The group of caspases, which includes caspases 1, 4, and 5, has been shown to prefer hydrophobic aromatic amino acids at position 4 on the N-terminal side of the cleavage site. Another group which includes caspases 2, 3 and 7, recognize aspartyl residues at both positions 1 and 4 on the N-terminal side of the cleavage site, and preferably a sequence of Asp-Glu-X-Asp. A third group, which includes caspases 6, 8, 9 and 10, tolerate many amino acids in the primary recognition sequence, but seem to prefer residues with branched, aliphatic side chains such as valine and leucine at position 4.

The caspases have also been grouped according to their perceived function. The first subfamily consists of caspases-1 (ICE), 4, and 5. These caspases have been shown to be involved in pro-inflammatory cytokine processing and therefore play an important role in inflammation. Caspase-1, the most studied enzyme of this class, activates the IL-1β precursor by proteolytic cleavage. This enzyme therefore plays a key role in the inflammatory response. Caspase-1 is also involved in the processing of interferon gamma inducing factor (IGIF or IL-18) which stimulates the production of interferon gamma, a key immunoregulator that modulates antigen presentation, T-cell activation and cell adhesion.

The remaining caspases make up the second and third subfamilies. These enzymes are of central importance in the intracellular signaling pathways leading to apoptosis. One subfamily consists of the enzymes involved in initiating events in the apoptotic pathway, including transduction of signals from the plasma membrane. Members of this subfamily include caspases-2, 8, 9 and 10. The other subfamily, consisting of the effector capsases 3, 6 and 7, are involved in the final downstream cleavage events that result in the systematic breakdown and death of the cell by apoptosis. Caspases involved in the upstream signal transduction activate the downstream caspases, which then disable DNA repair mechanisms, fragment DNA, dismantle the cell cytoskeleton and finally fragment the cell.

A four amino acid sequence primarily recognized by the caspases has been determined for enzyme substrates. Talanian et al., *J. Biol. Chem.* 272, 9677–9682, (1997); Thornberry et al., *J. Biol. Chem.* 272, 17907–17911, (1997). Knowledge of the four amino acid sequence primarily recognized by the caspases has been used to design caspase inhibitors. Reversible tetrapeptide inhibitors have been prepared having the structure $CH_3CO$—[P4]-[P3]-[P2]—$CH(R)CH_2CO_2H$ where P2 to P4 represent an optimal amino acid recognition sequence and R is an aldehyde, nitrile or ketone capable of binding to the caspase cysteine sulfhydryl. Rano and Thornberry, *Chem. Biol.* 4, 149–155 (1997); Mjalli, et al., *Bioorg. Med. Chem. Lett.* 3, 2689–2692 (1993); Nicholson et al., *Nature* 376, 37–43 (1995). Irreversible inhibitors based on the analogous tetrapeptide recognition sequence have been prepared where R is an acyloxymethylketone—$COCH_2OCOR'$. R' is exemplified by an optionally substituted phenyl such as 2,6-dichlorobenzoyloxy and where R is $COCH_2X$ where X is a leaving group such as F or Cl. Thornberry et al., *Biochemistry* 33, 3934 (1994); Dolle et al., *J Med. Chem.* 37, 563–564 (1994).

The utility of caspase inhibitors to treat a variety of mammalian disease states associated with an increase in cellular apoptosis has been demonstrated using peptidic caspase inhibitors. For example, in rodent models, caspase inhibitors have been shown to reduce infarct size and inhibit cardiomyocyte apoptosis after myocardial infarction, to reduce lesion volume and neurological deficit resulting from stroke, to reduce post-traumatic apoptosis and neurological deficit in traumatic brain injury, to be effective in treating fulminant liver destruction, and to improve survival after endotoxic shock. Yaoita et al., *Circulation*, 97, 276 (1998); Endres et al., *J Cerebral Blood Flow and Metabolism*, 18, 238, (1998); Cheng et al., J. Clin. Invest., 101, 1992 (1998); Yakovlev et al., *J Neuroscience*, 17, 7415 (1997); Rodriquez et al., *J. Exp. Med.*, 184, 2067 (1996); Grobmyer et al., *Mol. Med.*, 5, 585 (1999).

In general, the peptidic inhibitors described above are very potent against some of the caspase enzymes. However, this potency has not always been reflected in cellular models of apoptosis. In addition peptide inhibitors are typically characterized by undesirable pharmacological properties such as poor oral absorption, poor stability and rapid metabolism. Plattner and Norbeck, in *Drug Discovery Technologies*, Clark and Moos, Eds. (Ellis Horwood, Chichester, England, 1990).

There are reports of modified peptide inhibitors. WO 91/15577 and WO 93/05071 disclose peptide ICE inhibitors of the formula:

wherein Z is an N-terminal protecting group; $Q_2$ is 0 to 4 amino acids; and $Q_1$ is an electronegative leaving group.

WO 99/18781 discloses dipeptide caspase inhibitors of the formula:

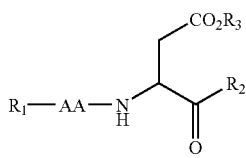

wherein $R_1$ is an N-terminal protecting group; AA is a residue of a natural α-amino acid or β-amino acid; $R_2$ is hydrogen or $CH_2R_4$ where $R_4$ is an electronegative leaving group; and $R_3$ is alkyl or hydrogen.

WO 99/47154 discloses dipeptide caspase inhibitors of the formula:

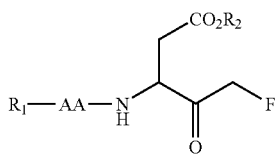

wherein $R_1$ is an N-terminal protecting group; AA is a residue of a non-natural α-amino acid or β-amino acid; and $R_2$ is optionally substituted alkyl or hydrogen.

WO 00/023421 discloses (substituted) acyl dipeptide apoptosis inhibitors having the formula:

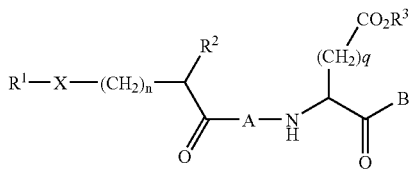

where n is 0, 1, or 2; q is 1 or 2; A is a residue of certain natural or non-natural amino acid; B is a hydrogen atom, a deuterium atom, $C_{1-10}$ straight chain or branched alkyl, cycloalkyl, phenyl, substituted phentyl, naphthyl, substituted naphthyl, 2-benzoxazolyl, substituted 2-oxazolyl, $(CH_2)_m$cycloalkyl, $(CH_2)_m$phenyl, $(CH_2)_m$(substituted phenyl), $(CH_2)_m$(1- or 2-naphthyl), $(CH_2)_m$heteroaryl, halomethyl, $CO_2R^{13}$, $CONR^{14}R^{15}$, $CH_2ZR^{16}$, $CH_2OCOaryl$, $CH_2OCO$(substituted aryl), $CH_2OCO$(heteroaryl), $CH_2OCO$(substituted heteroaryl), or $CH_2OPO(R^{17})R^{18}$, where $R^{13}$, $R^{14}$, $R^{15}$, $R^{16}$, $R^{17}$ and $R^{18}$ are defined in the application; $R^2$ is selected from a group containing hydrogen, alkyl, cycloalkyl, phenyl, substituted phenyl, $(CH_2)_m NH_2$; $R^3$ is hydrogen, alkyl, cycloalkyl, (cycloalkyl)alkyl, phenylalkyl, or substituted phenylalkyl; X is $CH_2$, C=O, O, S, NH, C=ONH or $CH_2OCONH$; and Z is an oxygen or a sulfur atom.

WO 97/24339 discloses inhibitors of interleukin-1β converter enzyme of the formula:

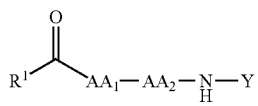

wherein $R^1$ represents H, alkyl, alkoxy, a carbocycle, a heterocycle, and various other groups; $AA^1$ and $AA^2$ are single bonds or amino acids; and Y represents a group of formula:

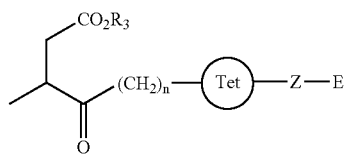

wherein the Tet ring represents a tetrazole ring; and Z represents, inter alia, alkylene, alkenylene, O, S, SO, and $SO_2$.

EP 618223 discloses ICE inhibitors of the formula:

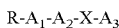

wherein R is H, a protecting group, or an optionally ring substituted $PhCH_2O$; $A_1$ is an α-hydroxy- or α-amino acid residue; $A_2$ is an α-hydroxyacid residue or α-amino acid or $A_1$ and $A_2$ form together a pseudodipeptide or a dipeptide mimetic residue; X is a residue derived from Asp wherein $A_3$ is $CH_2X_1COY_1$, $CH_2OY_2$, $CH_2SY_3$ or $CH_2$ $(CO)_mY_6$ wherein $X_1$ is O or S, m is 0 or 1 and $Y_1$, $Y_2$, $Y_3$ and $Y_6$ are optionally substituted cyclic aliphatic or aryl groups.

WO 98/16502 discloses, inter alia, ICE inhibitors of the formula:

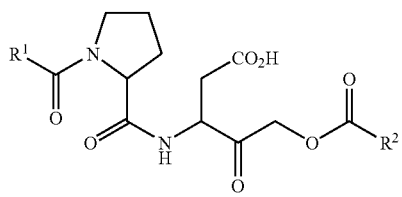

wherein $R_1$ and $R_2$ are as described in the application and the pyrrolidine ring is substituted by various groups.

While a number of caspase inhibitors have been reported, it is not clear whether they possess the appropriate pharmacological properties to be therapeutically useful. Therefore, there is a continued need for small molecule caspase inhibitors that are potent, stable, and penetrate membranes to provide effective inhibition of apoptosis in vivo. Such compounds would be extremely useful in treating the aforementioned diseases where caspase enzymes play a role.

SUMMARY OF THE INVENTION

It has now been found that compounds of this invention and pharmaceutical compositions thereof are effective as inhibitors of caspases and cellular apoptosis. These compounds have the general formula I:

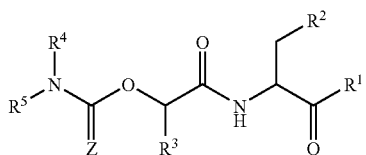

wherein:

Z is oxygen or sulfur;

$R^1$ is hydrogen, —$CHN_2$, —R, —$CH_2OR$, —$CH_2SR$, or —$CH_2Y$;

R is a $C_{1-12}$ aliphatic, aryl, aralkyl, heterocyclyl, or heterocyclylalkyl;

Y is an electronegative leaving group;

$R^2$ is $CO_2H$, $CH_2CO_2H$, or esters, amides or isosteres thereof;

$R^3$ is a group capable of fitting into the S2 sub-site of a caspase;

$R^4$ and $R^5$ taken together with the intervening nitrogen form a mono-, bi- or tricyclic hetero ring system having 1–6 heteroatoms selected from nitrogen, oxygen or sulfur.

The compounds of this invention have inhibition properties across a range of caspase targets with good efficacy in cellular models of apoptosis. In addition, these compounds will have good cell penetration and pharmacokinetic properties and, as a consequence of their potency, have good efficacy against diseases where caspases are implicated.

DETAILED DESCRIPTION OF THE INVENTION

This invention provides novel compounds, and pharmaceutically acceptable derivatives thereof, that are useful as caspase inhibitors. The invention also provides methods for using the compounds to inhibit caspase activity and to treat caspase-mediated disease states. These compounds have the general formula I:

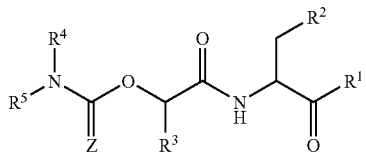

wherein:

Z is oxygen or sulfur;

$R^1$ is hydrogen, —$CHN_2$, —R, —$CH_2OR$, —$CH_2SR$, or —$CH_2Y$;

R is a $C_{1-12}$ aliphatic, aryl, aralkyl, heterocyclyl, or heterocyclylalkyl;

Y is an electronegative leaving group;

$R^2$ is $CO_2H$, $CH_2CO_2H$, or esters, amides or isosteres thereof;

$R^3$ is a group capable of fitting into the S2 sub-site of a caspase; and $R^4$ and $R^5$ taken together with the intervening nitrogen form a mono-, bi- or tricyclic hetero ring system having 1–6 heteroatoms selected from nitrogen, oxygen or sulfur.

As used herein, the following definitions shall apply unless otherwise indicated. The term "aliphatic" as used herein means straight chained or branched $C_1$–$C_{12}$ hydrocarbons which are completely saturated or which contain one or more units of unsaturation. For example, suitable aliphatic groups include substituted or unsubstituted linear, branched or cyclic alkyl, alkenyl, or alkynyl groups and hybrids thereof such as (cycloalkyl)alkyl, (cycloalkenyl) alkyl or (cycloalkyl)alkenyl. The term "alkyl" used alone or as part of a larger moiety refers to both straight and branched chains containing one to twelve carbon atoms. When the term alkyl is used as part of a larger moiety, as in aralkyl or heteroaralkyl, the alkyl portion will preferably contain one to six carbons. The term "halogen" means F, Cl, Br, or I. The term "aryl" refers to monocyclic or polycyclic aromatic ring groups having five to fourteen atoms, such as phenyl, naphthyl and anthryl. The term "heterocyclic group" refers to saturated and unsaturated monocyclic or polycyclic ring systems containing one or more heteroatoms and a ring size of three to nine such as furanyl, thienyl, pyrrolyl, pyrrolinyl, pyrrolidinyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridinyl, piperidinyl, dioxanyl, morpholinyl, dithianyl, thiomorpholinyl, pyridazinyl, pyrimidinyl, pyrazinyl, piperazinyl, triazinyl, trithianyl, indolizinyl, indolyl, isoindolyl, indolinyl, benzofuranyl, benzothiophenyl, indazolyl, benzimidazolyl, benzthiazolyl, purinyl, quinolizinyl, quinolinyl, isoquinolinyl, cinnolinyl, phthalazinyl, quinazolinyl, quinoxalinyl, 1,8-naphthyridinyl, pteridinyl, quinuclidinyl, carbazolyl, acridinyl, phenazinyl, phenothiazinyl, or phenoxazinyl. "Heteroaryl" refers to a heterocyclic ring that is aromatic. It is understood that the compounds of this invention are limited to those that can exist in nature as stable chemical compounds.

The term "carbocyclic group" refers to saturated monocyclic or polycyclic carbon ring systems of three to fourteen carbons which may be fused to aryl or heterocyclic groups. Examples include cyclohexyl, cyclopentyl, cyclobutyl, cyclopropyl, indanyl, tetrahydronaphthyl and the like.

An aliphatic, alkyl, aryl, heteroaryl, heterocyclyl, or carbocyclyl, used alone or as part of a larger moiety, refers to substituted or unsubstituted groups. When substituted, these groups may contain one or more substituents. Examples of suitable substituents include halogen, —R, —OR, —OH, —SH, —SR, protected OH (such as acyloxy), phenyl (Ph), substituted Ph, —OPh, substituted —OPh, —$NO_2$, —CN, —$NH_2$, —NHR, —$N(R)_2$, —NHCOR, —NHCONHR, —$NHCON(R)_2$, —NRCOR, —$NHCO_2R$, —$CO_2R$, —$CO_2H$, —COR, —CONHR, —$CON(R)_2$, —$S(O)_2R$, —$SONH_2$, —S(O)R, —$SO_2NHR$, —$NHS(O)_2R$, =O, =S, =NNHR, =$NNR_2$, =N—OR, =NNHCOR, =$NNHCO_2R$, =$NNHSO_2R$, or =NR where R is an aliphatic group or a substituted aliphatic group.

A substitutable nitrogen on a heterocyclic ring may be optionally substituted. Suitable substituents on the nitrogen include R, COR, $S(O)_2R$, and $CO_2R$, where R is an aliphatic group or a substituted aliphatic group.

Nitrogen and sulfur may be in their oxidized form, and nitrogen may be in a quaternized form.

The term "electronegative leaving group" has the definition known to those skilled in the art (see March, *Advanced Organic Chemistry*, 4th Edition, John Wiley & Sons, 1992). Examples of electronegative leaving groups include halogens such as F, Cl, Br, I, aryl, and alkylsulfonyloxy groups, trifluoromethanesulfonyloxy, OR, SR, —OC=O(R), —OPO($R^6$) ($R^7$), where R is an aliphatic group, an aryl group, an aralkyl group, a carbocyclic group, an alkyl carbocyclic group, a heterocyclic group, or an alkyl heterocyclic group; and $R^6$ and $R^7$ are independently selected from R or OR.

When the $R^2$ group is in the form of an ester or amide, the present compounds undergo metabolic cleavage to the corresponding carboxylic acids, which are the active caspase inhibitors. Because they undergo metabolic cleavage, the precise nature of the ester or amide group is not critical to the working of this invention. The structure of the $R^2$ group may range from the relatively simple diethyl amide to a steroidal ester. Examples of esters of $R^2$ carboxylic acids include, but are not limited to, $C_{1-12}$ aliphatic, such as $C_{1-6}$ alkyl or $C_{3-10}$ cycloalkyl, aryl, such as phenyl, aralkyl, such as benzyl or phenethyl, heterocyclyl or heterocyclylalkyl. Examples of suitable $R^2$ heterocyclyl rings include, but are not limited to, 5–6 membered heterocyclic rings having one or two heteroatoms such as piperidinyl, piperazinyl, or morpholinyl.

Amides of $R^2$ carboxylic acids may be primary, secondary or tertiary. Suitable substituents on the amide nitrogen include, but are not limited to, one or more groups independently selected from the aliphatic, aryl, aralkyl, heterocyclyl or heterocyclylalkyl groups described above for the $R^2$ ester alcohol. Likewise, other prodrugs are included within the scope of this invention. See Bradley D. Anderson, "Prodrugs for Improved CNS Delivery" in Advanced Drug Delivery Reviews (1996), 19, 171–202.

Isosteres or bioisosteres of $R^2$ carboxylic acids, esters and amides result from the exchange of an atom or group of atoms to create a new compound with similar biological properties to the parent carboxylic acid or ester. The bioisosteric replacement may be physicochemically or topologically based. An example of an isosteric replacement for a carboxylic acid is $CONHSO_2$(alkyl) such as $CONHSO_2Me$.

$R^3$ may be any group capable of fitting into the S2 sub-site of a caspase. Such groups are known from the many caspase inhibitors that have been reported (see WO91/15577, WO93/05071, WO99/18781, WO99/47154, WO00/023421, WO9724339, EP618223, WO9816502, all of which are described above). Furthermore, the structures of several of the caspase enzymes including the S-2 subsites are also known. References to the caspase structure include the following: Blanchard H, et al., *J. Mol. Biol.* 302(1), 9–16 (2000); Wei Y, et al., *Chem. Biol.* 7(6):423–32 (2000); Lee D, et al., *J Biol. Chem.* 275(21):16007–14 (2000); Blanchard H, et al., *Structure Fold Des.* 7(9):1125–33 (1999); Okamoto Y, et al, *Chem. Pharm. Bull.* (Tokyo) 47(1):11–21 (1999); Margolin N, et al, *J. Biol. Chem.* 272(11):7223–8 (1997); Walker N P, et al., *Cell* 78(2):343–52 (1994); and Wilson K P, et al., *Nature* 370(6487):270–5 (1994).

Whether a group will fit into the S-2 subsite will depend on the particular caspase that is being considered. The size of the subsite will range from the small S-2 subsite of caspase-3 which permits a group up to the size of a $C_4$ aliphatic group to a relatively large subsite which permits a group having a molecular weight up to about 140 Daltons, such as a naphthyl group. The size, along with the electronic nature, of the $R^3$ group will influence the caspase selectivity of the inhibitor. From the references provided above, one skilled in the art could readily ascertain whether a group is capable of fitting favorably into an S-2 subsite of a caspase, for example, by using standard molecular modeling programs such as Quanta or Macromodel.

$R^3$ groups include those that are selected from hydrogen, a side chain of a natural α-amino acid, or a substituted or unsubstituted group having a molecular weight up to about 140 Daltons selected from aliphatic, aryl, aralkyl, heterocyclyl, and heterocyclylalkyl groups. Examples of $R^3$ aliphatic groups include methyl, ethyl, propyl, isopropyl, cyclopropyl, butyl, isobutyl, sec-butyl, tert-butyl, cyclobutyl, pentyl, cyclopentyl, hexyl, and cyclohexyl. Examples of $R^3$ aryl groups include phenyl, indenyl and naphthyl. Examples of $R^3$ heterocyclic groups include pyrrolidinyl, pyrrolinyl, imidazolidinyl, imidazolinyl, pyrazolinyl, pyrazolidinyl, piperidinyl, morpholinyl, thiomorpholinyl, piperazinyl, homopiperidinyl, and quinuclidinyl. Examples of $R^3$ heteroaryl groups include furanyl, thienyl, pyrrolyl, oxazole, thiazolyl, imidazolyl, pyrazolyl, isoxazolyl, isothiazolyl, oxadiazolyl, furazanyl, triazolyl, thiadiazolyl, pyridinyl, pyridazinyl, pyrimidinyl, pyrazinyl, triazinyl, indolyl, isoindolyl, indolinyl, benzofuranyl, benzothiophene, indazolyl, benzimidazolyl, benzthiazolyl, purinyl, quinolinyl, isoquinolinyl, quinolizinyl, cinnolinyl, phthalazinyl, quinazolinyl, quinoxalinyl, naphthyridinyl, pteridinyl, chromanyl, and isochromanyl. Each group may contain one or more substituents, as described above.

$R^4$ and $R^5$ taken together with the intervening nitrogen form mono-, bi- or tricyclic hetero ring system having 1–6 heteroatoms, preferably 1–4 heteroatoms. Such rings include substituted or unsubstituted indole, isoindole, indoline, indazole, purine, dihydropyridine, benzimidazole, imidazole, imidazoline, pyrrole, pyrrolidine, pyrroline, pyrazole, pyrazoline, pyrazolidine, triazole, piperidine, morpholine, thiomorpholine, piperazine, carbazole, phenothiazine, phenoxazine, dihydrophenazine, dihydrocinnoline, dihydroquinoxaline, tetrahydroquinoline, tetrahydroisoquinoline, dihydronaphthyridine, tetrahydronaphthyridine, dihydroacridine, 5H-dibenzo[b,f] azepine, 10,11-dihydro-5H-dibenzo[b,f]azepine, β-carboline, pyrido[4,3-b]indole, 2,3,9-triazafluorene, 9-thia-2,10-diazaanthracene, 3,6,9-triazafluorene, thieno[3,2-b]pyrrole, or dihydrophenanthridine. Suitable substituents on $R^4$ or $R^5$ include one or more groups independently selected from a halogen, —R, —OR, —OH, —SH, —SR, protected OH (such as acyloxy), phenyl (Ph), substituted Ph, —OPh, substituted —OPh, —$NO_2$, —CN, —$NH_2$, —NHR, —N(R)$_2$, —NHCOR, —NHCONHR, —NHCON(R)$_2$, —NRCOR, —NHCO$_2$R, —CO$_2$R, —CO$_2$H, —COR, —CONHR, —CON(R)$_2$, —S(O)$_2$R, —SONH$_2$, —S(O)R, —SO$_2$NHR, or —NHS(O)$_2$R, where each R is independently selected from an aliphatic group or a substituted aliphatic group.

Compounds of this invention where $R^2$ is COOH are gamma-ketoacids, which may exist in solution as either the open form 1 or the cyclized hemiketal form 2. The representation herein of either isomeric form is meant to include the other. Similarly, cyclization may also occur where $R^2$ is $CH_2COOH$, and such cyclized isomers are understood to be included when the ring open form is represented herein.

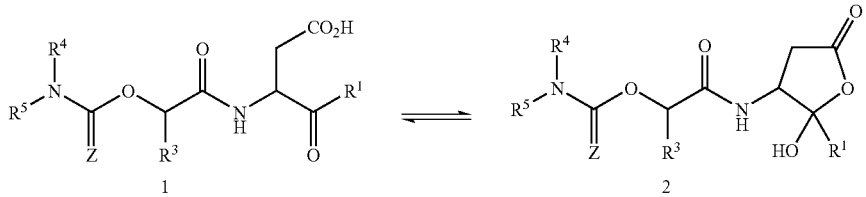

Likewise it will be apparent to one skilled in the art that certain compounds of this invention may exist in tautomeric forms or hydrated forms, all such forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are within the scope of this invention.

One embodiment of this invention relates to compounds that have one or more, and preferably all, of the following features:

(i) Z is oxygen.
(ii) $R^1$ is hydrogen, —R, —$CH_2OR$, —$CH_2SR$, or —$CH_2Y$. More preferably, $R^1$ is —$CH_2OR$, —$CH_2SR$, or —$CH_2Y$. An even more preferred $R^1$ is —$CH_2Y$. Most preferably, $R^1$ is —$CH_2F$.
(iii) $R^2$ is $CO_2H$ or an ester, amide or isostere thereof.
(iv) $R^3$ is a group having a molecular weight up to about 140 Daltons, such as an aliphatic or aralkyl group. More preferably, $R^3$ is a $C_1$–$C_4$ alkyl which is a group that fits into the S2 subsite of a range of caspases.
(v) $R^4$ and $R^5$ taken together with the intervening nitrogen form a monocyclic, bicyclic or tricyclic heterocyclic or heteroaryl ring system wherein each ring of the system has 5–7 ring atoms.

A key feature of the present compounds is the hetero ring system formed by taking $R^4$ and $R^5$ together with the intervening nitrogen. Bicyclic or tricyclic heterocyclic or heteroaryl rings are preferred over monocyclic rings. Accordingly, a preferred embodiment relates to compounds having one or more, and preferably all, of the following features: (i) Z is oxygen; (ii) $R^1$ is hydrogen, —R, —$CH_2OR$, —$CH_2SR$, or —$CH_2Y$, more preferably, $R^1$ is —$CH_2OR$, —$CH_2SR$, or —$CH_2Y$, more preferably, $R^1$ is —$CH_2Y$, and most preferably, $R^1$ is —$CH_2F$; (iii) $R^2$ is $CO_2H$ or an ester, amide or isostere thereof; (iv) $R^3$ is a group having a molecular weight up to about 140 Daltons, such as an aliphatic or aralkyl group, more preferably a $C_{1-4}$ alkyl group; and/or (v) $R^4$ and $R^5$ taken together with the intervening nitrogen form a bicyclic or tricyclic heterocyclic or heteroaryl ring system wherein each ring of the system has 5–7 ring atoms.

Examples of preferred monocyclic rings include triazole, piperidine, morpholine, thiomorpholine, imidazole, pyrrolidine, pyrazole, and piperazine. Examples of preferred bicyclic rings include indole, isoindole, indoline, indazole, benzimidazole, thieno[3,2-b]pyrrole, dihydroquinoxaline, dihydrocinnoline, dihydronaphthyridine, tetrahydronaphthyridine, tetrahydroquinoline, and tetrahydroisoquinoline, most preferably indole or indoline. Examples of preferred tricyclic rings include carbazole, phenothiazine, β-carboline, pyrido[4,3-b]indole, 2,3,9-triazafluorene, 9-thia-2,10-diazaanthracene, 3,6,9-triazafluorene, phenoxazine, dibenzoazepine, dihydro-dibenzoazepine, dihydrophenazine, dihydroacridine, or dihydrophenanthridine, most preferably carbazole, phenothiazine or dihydrophenanthridine.

Specific examples of compounds I are shown in Table 1.

TABLE 1

Examples of Formula I compounds (Z is oxygen)

| No. | Structure |
|---|---|
| 1 | 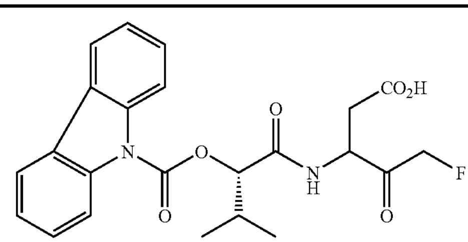 |

TABLE 1-continued
Examples of Formula I compounds (Z is oxygen)
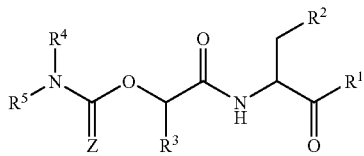
| No. | Structure |
|---|---|
| 2 | |
| 3 | |
| 4 | |
| 5 | |
| 6 | |

TABLE 1-continued
Examples of Formula I compounds (Z is oxygen)
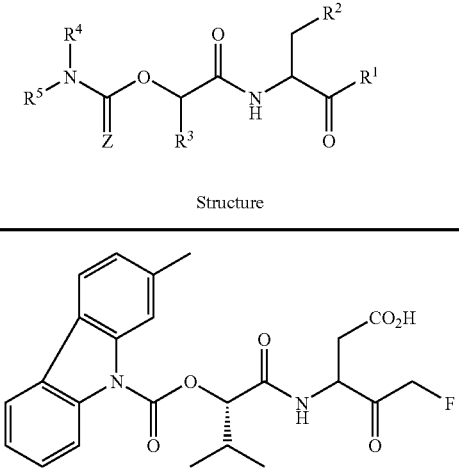
| No. | Structure |
|---|---|
| 7 | 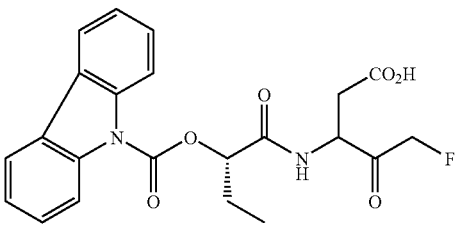 |
| 8 | 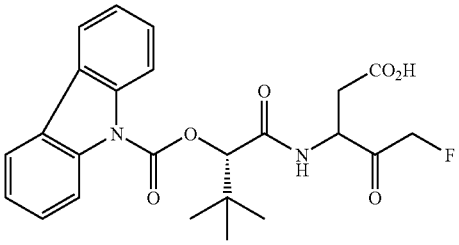 |
| 9 | 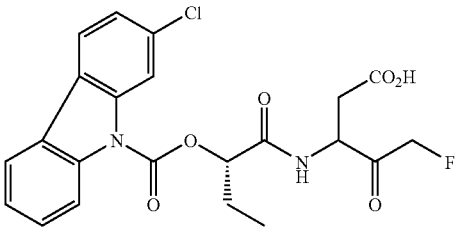 |
| 10 | 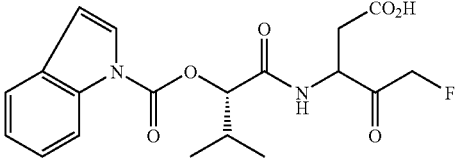 |
| 11 | 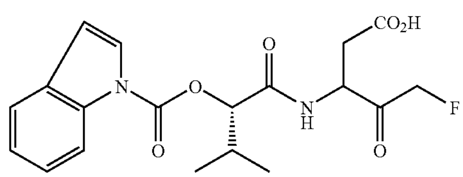 |

TABLE 1-continued

Examples of Formula I compounds (Z is oxygen)

| No. | Structure |
|-----|-----------|
| 12  | (phenothiazine-N-C(O)O-CH(iPr)-C(O)NH-CH(CH2CO2H)-C(O)CH2F) |
| 13  | (2-chloro-phenothiazine-N-C(O)O-CH(iPr)-C(O)NH-CH(CH2CO2H)-C(O)CH2F) |
| 14  | (3-chloro-phenothiazine-N-C(O)O-CH(iPr)-C(O)NH-CH(CH2CO2H)-C(O)CH2F) |
| 15  | (2,8-dichloro-phenothiazine-N-C(O)O-CH(iPr)-C(O)NH-CH(CH2CO2H)-C(O)CH2F) |
| 16  | (1,2-dichloro-phenothiazine-N-C(O)O-CH(iPr)-C(O)NH-CH(CH2CO2H)-C(O)CH2F) |

TABLE 1-continued
Examples of Formula I compounds (Z is oxygen)
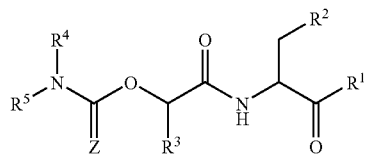
| No. | Structure |
|---|---|
| 17 | 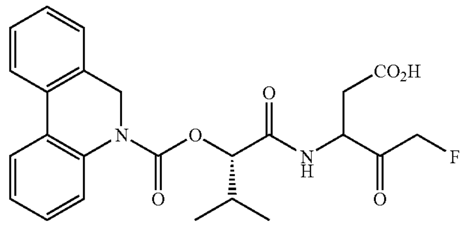 |
| 18 | 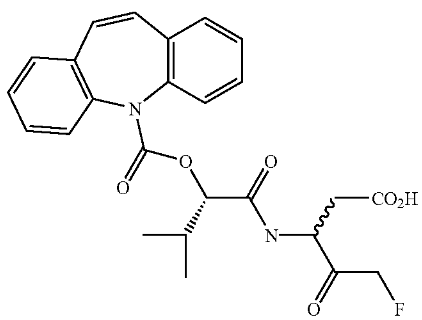 |
| 19 | 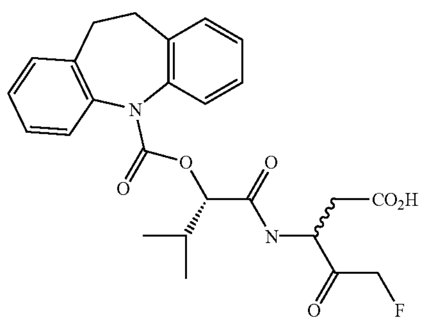 |
| 20 | 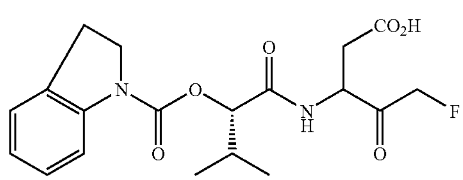 |
| 21 | 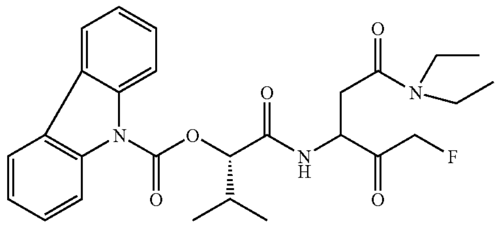 |

TABLE 1-continued

Examples of Formula I compounds (Z is oxygen)

| No. | Structure |
|-----|-----------|
| 22  | 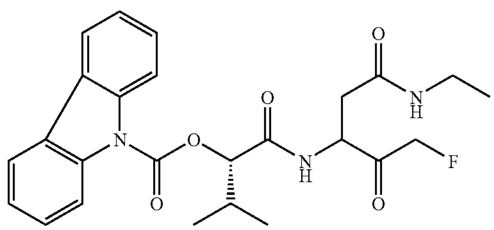 |
| 23  | 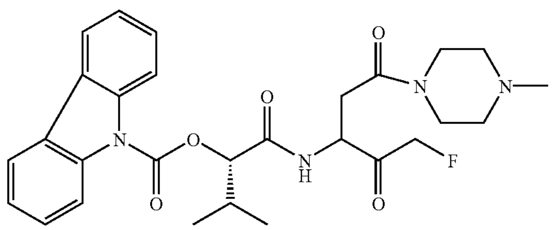 |
| 24  | 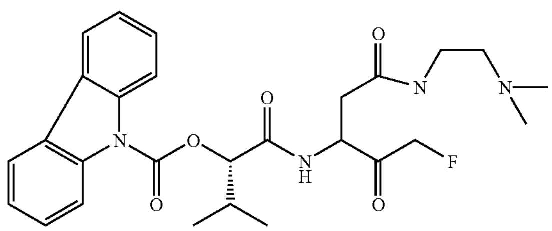 |
| 25  | 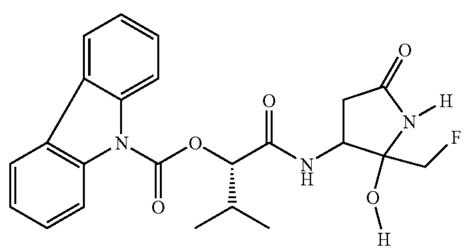 |
| 26  | 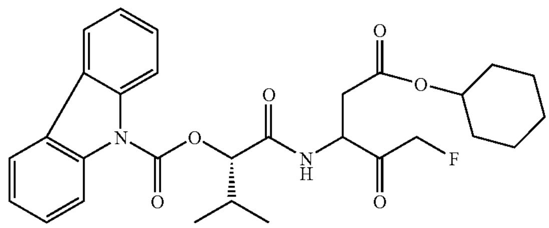 |

TABLE 1-continued
Examples of Formula I compounds (Z is oxygen)
| No. | Structure |
|---|---|
| 27 | 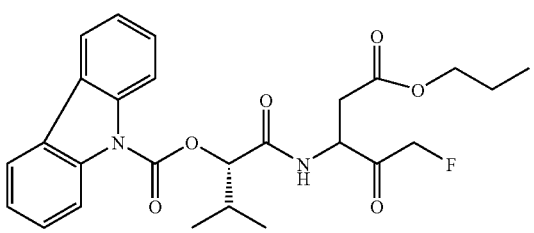 |
| 28 | 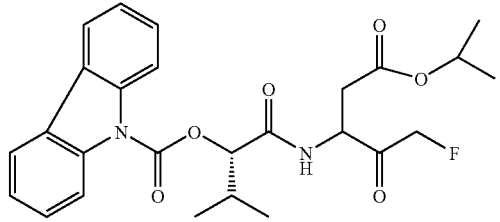 |
| 29 | 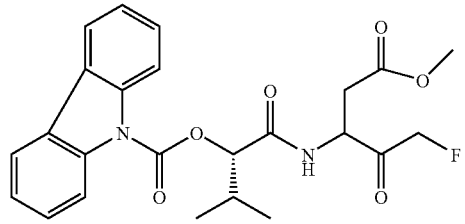 |
| 30 | 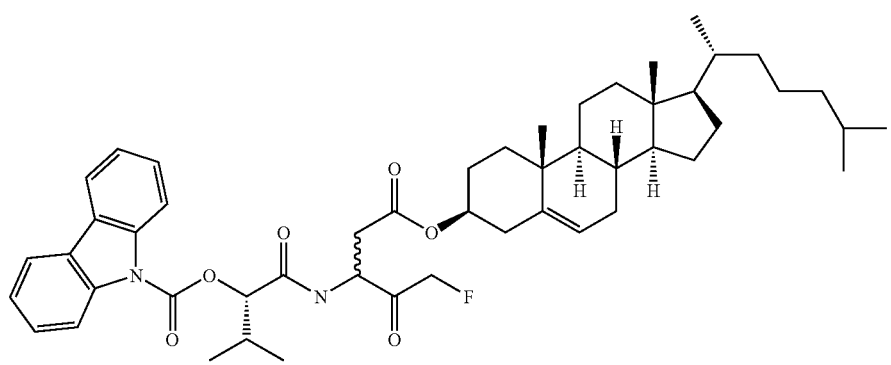 |
| 31 | 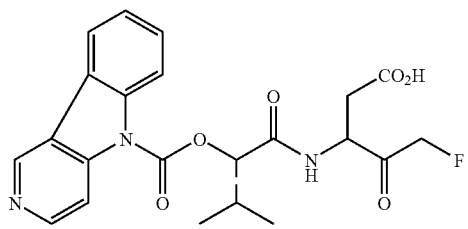 |

TABLE 1-continued

Examples of Formula I compounds (Z is oxygen)

| No. | Structure |
|---|---|
| 32 | 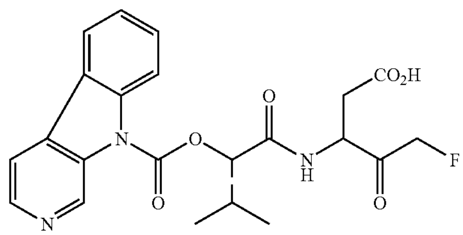 |
| 33 | 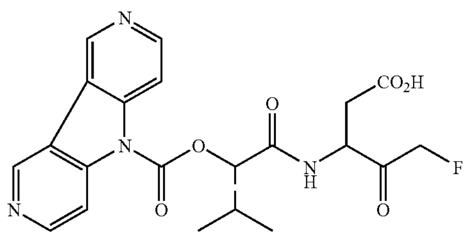 |
| 34 | 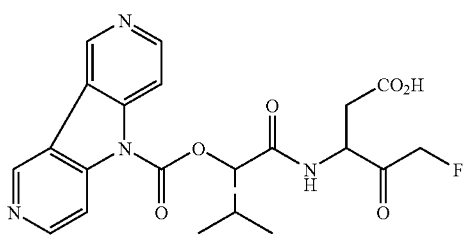 |
| 35 | 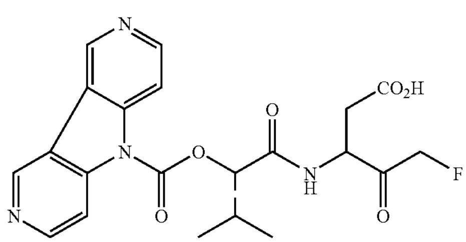 |
| 36 | 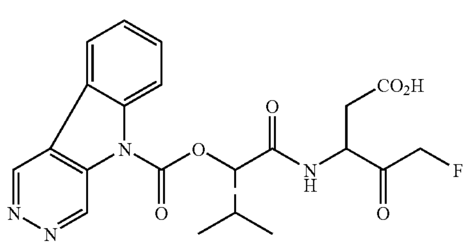 |

TABLE 1-continued

Examples of Formula I compounds (Z is oxygen)

| No. | Structure |
|---|---|
| 37 | 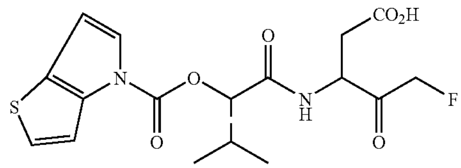 |
| 38 | 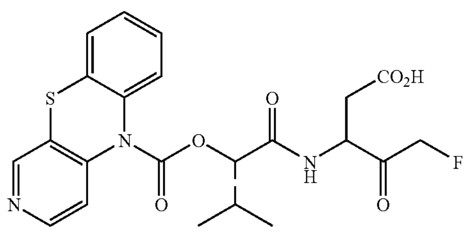 |
| 39 | 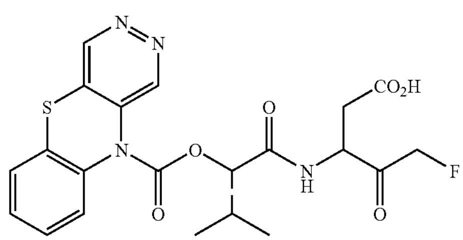 |
| 40 | 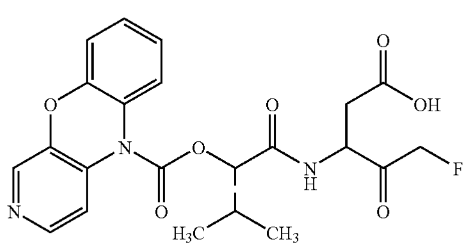 |
| 41 | 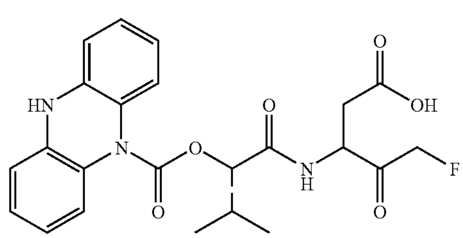 |

TABLE 1-continued
Examples of Formula I compounds (Z is oxygen)
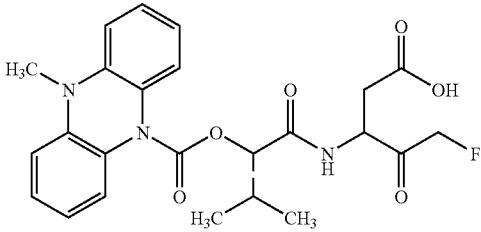
| No. | Structure |
| --- | --- |
| 42 | 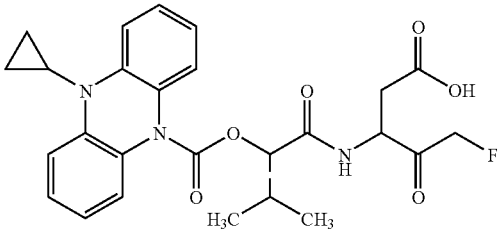 |
| 43 | 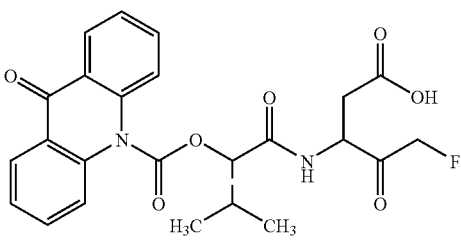 |
| 44 | 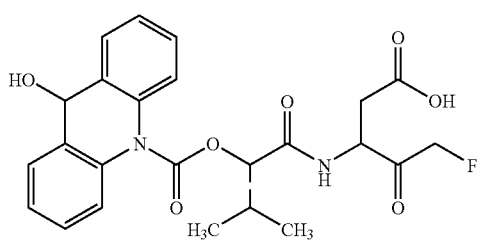 |
| 45 | 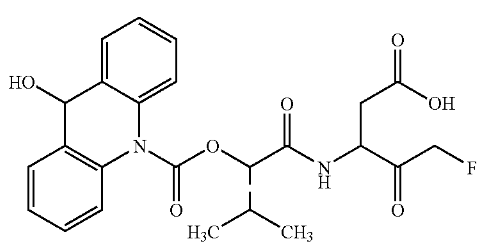 |

TABLE 1-continued

Examples of Formula I compounds (Z is oxygen)

| No. | Structure |
|-----|-----------|
| 46 | (structure with sulfone-containing tricyclic ring) |
| 47 | (structure with sulfoxide-containing tricyclic ring) |
| 48 | (structure with N-acetyl phenazine-type tricyclic ring) |

After evaluating many $R^4$—N—$R^5$ heterocyclic rings, it was found that tricyclic compounds where the end rings are substantially co-planar show surprisingly superior broad caspase activity compared to acyclic analogs or other tricyclic ring systems that are not substantially co-planar. This substantial co-planarity can be achieved when the middle ring of the tricyclic ring system is a 5- or 6-membered ring, such as in a carbazole or phenothiazine ring.

Furthermore, these substantially co-planar tricyclic ring systems, as well as bicyclic ring systems such as indole and indoline, confer better broad caspase activity that the corresponding compounds where the $R^4$—N—$R^5$ heterocyclic ring is monocyclic such as piperidine, piperazine or morpholine.

Accordingly, a preferred embodiment of this invention relates to compounds of formula I where $R^4$—N—$R^5$ is a tricyclic ring system having 1–6 heteroatoms, preferably 1–4 heteroatoms, selected from nitrogen, oxygen or sulfur wherein the end rings of the ring system have 5–7 ring atoms and the middle ring has 5 or 6 ring atoms.

One aspect of this embodiment relates to compounds of formula II:

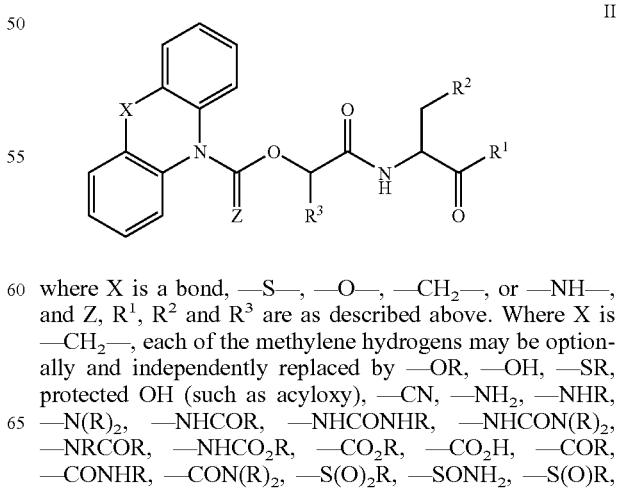

where X is a bond, —S—, —O—, —CH$_2$—, or —NH—, and Z, $R^1$, $R^2$ and $R^3$ are as described above. Where X is —CH$_2$—, each of the methylene hydrogens may be optionally and independently replaced by —OR, —OH, —SR, protected OH (such as acyloxy), —CN, —NH$_2$, —NHR, —N(R)$_2$, —NHCOR, —NHCONHR, —NHCON(R)$_2$, —NRCOR, —NHCO$_2$R, —CO$_2$R, —CO$_2$H, —COR, —CONHR, —CON(R)$_2$, —S(O)$_2$R, —SONH$_2$, —S(O)R, —SO$_2$NHR, —NHS(O)$_2$R, =O, =S, =NNHR, =NNR$_2$, =N—OR, =NNHCOR, =NNHCO$_2$R, =NNHSO$_2$R, or =NR where R is a C$_{1-4}$ aliphatic group. Where X is —NH—, the NH hydrogen may be replaced by alkyl, CO(alkyl), CO$_2$(alkyl), or SO$_2$(alkyl). Preferred groups for R$^1$, R$^2$ and R$^3$ are as described above.

The compounds of this invention may be prepared in general by methods known to those skilled in the art for analogous compounds, as illustrated by the general schemes below and by the preparative examples that follow.

carboxylic acid, then R$^2$ in 6 is preferably an ester and the final step in the scheme is a hydrolysis.

Starting isocyanates or thioisocyanates 1 are commercially available or may be made by reaction of an amine with phosgene or a phosgene equivalent (or thiophosgene for preparation of thioisocyanates) in the presence of a base such as triethylamine. The lactate derivatives are commercially available or may be made by reaction of an amino acid with a diazotization reagent such as with NaNO$_2$.

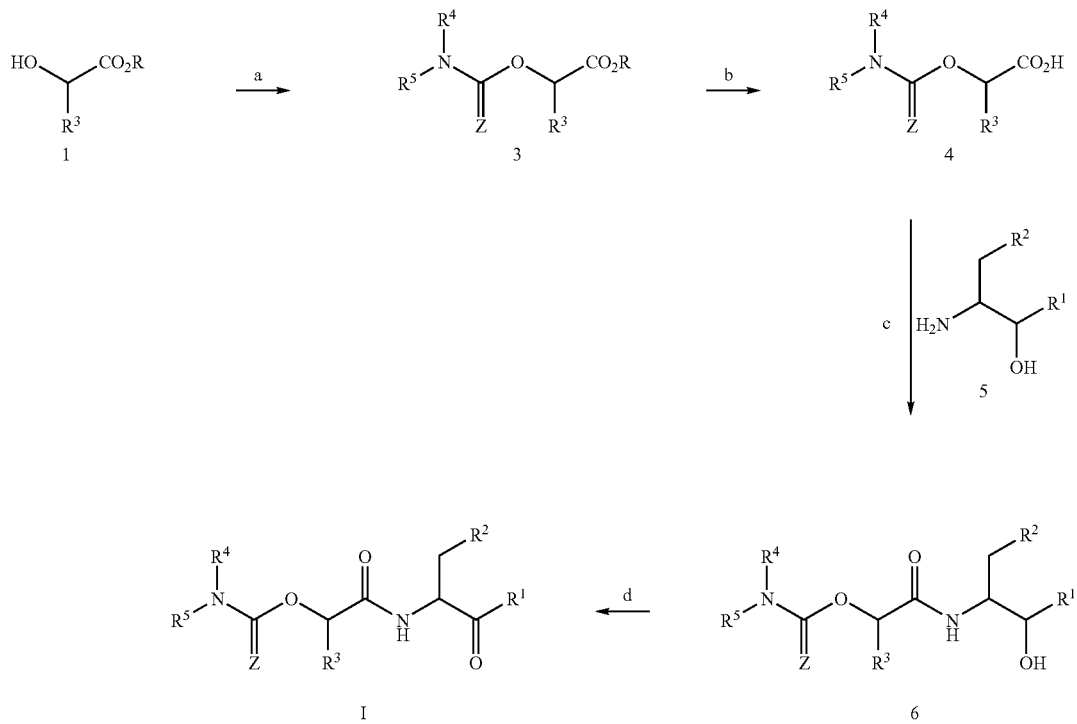

Scheme I

Reagents: (a) R$^5$—N=C=Z (2);
(b) NaOH/THF/H$_2$O;
(c) EDC/DMAP/HOBt;
(d) i. Dess-Martin periodinane, (ii) TFA/DCM Scheme I above shows a synthetic route for obtaining compounds where R$^4$ is a hydrogen. Reaction of an isocyanate or thioisocyanate 2 with a lactic acid derivative 1 produces carbamate 3. The ester group of 3 is hydrolyzed using base or, when the ester is a t-butyl group, using trifluoroacetic acid to provide the acid 4, which is then coupled with the amino alcohol 5. Depending on the nature of R$^1$ and R$^2$ an amino ketone may be used, in place of the amino alcohol, which avoids the subsequent oxidation step. In the case of fluoromethyl ketones where R$^1$ is CH$_2$F, the amino alcohol 5 may be obtained according to the method of Revesz et al., *Tetrahedron Lett.*, 1994, 35, 9693. Finally the hydroxyl group in compound 6 is oxidized and the resulting compound treated appropriately according to the nature of R$^2$. For example, if the product I requires R$^2$ to be a

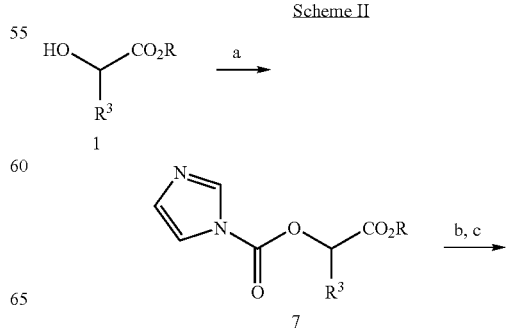

Scheme II

-continued

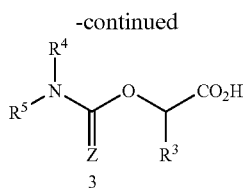

Reagents: (a) CDI/THF;
(b) MeOTf/CH$_2$Cl$_2$;
(c) R$^4$R$^5$NH(8)/THF.

Scheme II above shows a synthetic route for obtaining compounds I of this invention where R$^4$ is an alkyl group or when R$^4$ and R$^5$ together form a ring. Reaction of the lactate derivative 2 with 1,1'-carbonyldiimidazole (CDI) gives the imidazolate 7. Methylation of 7 by methyl triflate, followed by reaction with amine 8 (see *J. Med. Chem.*, (1996), 39, 982) provides the intermediate 3. Scheme I above shows how 3 may be converted to I.

Scheme III

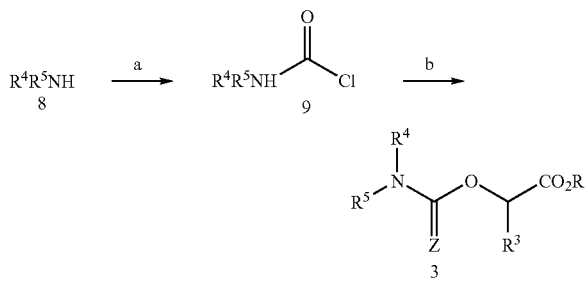

Reagents: (a) COCl$_2$/CH$_2$Cl$_2$;
(b) 1/THF.

An alternative synthetic route for obtaining compounds I of this invention where R$^4$ is an alkyl group or when R$^4$ and R$^5$ together form a ring is shown in Scheme III above. Treatment of amine 8 with phosgene gives a carbamoyl chloride intermediate 9. Reaction of 9 with lactate derivative 1 provides intermediate 3.

Scheme IV

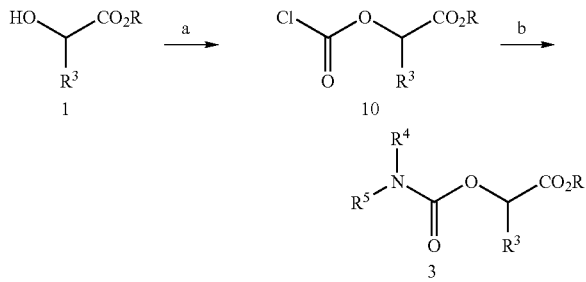

Reagents: (a) Cl$_3$COC(O)Cl/THF;
(b) R$_4$R$_5$NH(8), NaOH, Bu$_4$NBr.

Scheme IV above shows a synthetic route for obtaining compounds of this invention where R$^4$ is a hydrogen or an alkylgroup or when R$^4$ and R$^5$ together form a ring. Reaction of hydroxy ester 1 with phosgene or a phosgene equivalent such as diphogene or triphosgene leads to chloroformate intermediate 10. Reaction of 10 with amine 8 provides intermediate 3.

The compounds of this invention are designed to inhibit caspases. Therefore, the compounds of this invention may be assayed for their ability to inhibit apoptosis, the release of IL-1β or caspase activity directly. Assays for each of the activities are described below in the Testing section and are also known in the art.

One embodiment of this invention relates to a composition comprising a compound of formula I or a pharmaceutically acceptable salt thereof, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intraarticular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The above-described compositions are particularly useful in therapeutic applications relating to an IL-1 mediated disease, an apoptosis mediated disease, an inflammatory disease, an autoimmune disease, a destructive bone disorder, a proliferative disorder, an infectious disease, a degenerative disease, a disease associated with cell death, an excess dietary alcohol intake disease, a viral mediated disease, uveitis, inflammatory peritonitis, osteoarthritis, pancreatitis, asthma, adult respiratory distress syndrome, glomerulonephritis, rheumatoid arthritis, systemic lupus erythematosus, scleroderma, chronic thyroiditis, Grave's disease, autoimmune gastritis, diabetes, autoimmune hemolytic anemia, autoimmune neutropenia, thrombocytopenia, chronic active hepatitis, myasthenia gravis, inflammatory bowel disease, Crohn's disease, psoriasis, atopic dermatitis, scarring, graft vs host disease, organ transplant rejection, osteoporosis, leukemias and related disorders, myelodysplastic syndrome, multiple myeloma-related bone disorder, acute myelogenous leukemia, chronic myelogenous leukemia, metastatic melanoma, Kaposi's sarcoma, multiple myeloma, haemorrhagic shock, sepsis, septic shock, burns, Shigellosis, Alzheimer's disease, Parkinson's disease, Huntington's disease, Kennedy's disease, prion disease, cerebral ischemia,epilepsy, myocardial ischemia, acute and chronic heart disease, myocardial infarction, congestive heart failure, atherosclerosis, coronary artery bypass graft, spinal muscular atrophy, amyotrophic lateral sclerosis, multiple sclerosis, HIV-related encephalitis, aging, alopecia, neurological damage due to stroke, ulcerative colitis, traumatic brain injury, spinal cord injury, hepatitis-B, hepatitis-C, hepatitis-G, yellow fever, dengue fever, or Japanese encephalitis, various forms of liver disease, renal disease, polyaptic kidney disease, *H. pylori*-associated gastric and duodenal ulcer disease, HIV infection, tuberculosis, and meningitis. The compounds and compositions are also useful in treating complications associated with coronary artery bypass grafts and as a component of immunotherapy for the treatment of various forms of cancer.

The amount of compound present in the above-described compositions should be sufficient to cause a detectable decrease in the severity of the disease or in caspase activity and/or cell apoptosis, as measured by any of the assays described in the examples.

The compounds of this invention are also useful in methods for preserving cells, such as may be needed for an organ transplant or for preserving blood products. Similar uses for caspase inhibitors have been reported (Schierle et al., *Nature Medicine*, 1999, 5, 97). The method involves treating the cells or tissue to be preserved with a solution comprising the caspase inhibitor. The amount of caspase inhibitor needed will depend on the effectiveness of the inhibitor for the given cell type and the length of time required to preserve the cells from apoptotic cell death.

According to another embodiment, the compositions of this invention may further comprise another therapeutic agent. Such agents include, but are not limited to, thrombolytic agents such as tissue plasminogen activator and streptokinase. When a second agent is used, the second agent may be administered either as a separate dosage form or as part of a single dosage form with the compounds or compositions of this invention.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and other therapeutic agent, if present, in the composition.

In a preferred embodiment, the invention provides a method of treating a mammal, having one of the aforementioned diseases, comprising the step of administering to said mammal a pharmaceutically acceptable composition described above. In this embodiment, if the patient is also administered another therapeutic agent or caspase inhibitor, it may be delivered together with the compound of this invention in a single dosage form, or, as a separate dosage form. When administered as a separate dosage form, the other caspase inhibitor or agent may be administered prior to, at the same time as, or following administration of a pharmaceutically acceptable composition comprising a compound of this invention.

In order that this invention be more fully understood, the following preparative and testing examples are set forth. These examples are for the purpose of illustration only and are not to be construed as limiting the scope of the invention in any way.

SYNTHESIS EXAMPLES

The following Examples provide synthetic procedures for selected compounds of this invention.

Example 1

[3S/R]-5-Fluoro-4-oxo-3-[(S)-3-methyl-2-(carbazole-carbamoyloxy-butyrylamino]-pentanoic acid

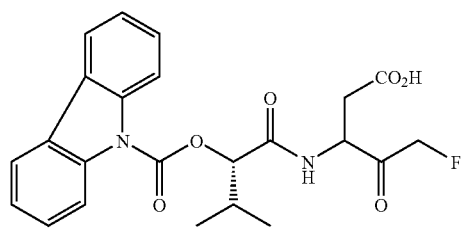

Method A:

(S)-2-(chlorocarbamoyloxy)-3-methylbutyric acid, tert-butyl ester

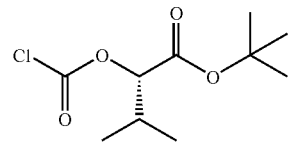

To a solution of diphosgene (4.55 g) in THF (34 ml) at 0° C. was added a solution of (S)-2-hydroxy-3-methylbutyric acid tert-butyl ester (for preparation method see *Tetrahedron. Lett.*, (1993), 7409) (4.0 g) and pyridine (1.82 g) in THF (34 ml) dropwise over 25 minutes. The resulting mixture was allowed to warm to room temperature over 4 hours. The mixture was then filtered through celite and the filtrate concentrated under reduced pressure. The residue was re-dissolved in diethyl ether (200 ml) and again filtered through celite. The filtrate was concentrated under reduced pressure to give the sub-title compound as a pale yellow oil (5.27 g): $^1$H NMR (400 MHz, CDCl$_3$) δ 0.98–1.10 (6H, m), 1.55 (9H, s), 2.30 (1H, m), 4.83 (1H, m).

Method B:

(S)-3-methyl-2-(carbazole-carbamoyloxy)-butyric acid, tert-butyl ester

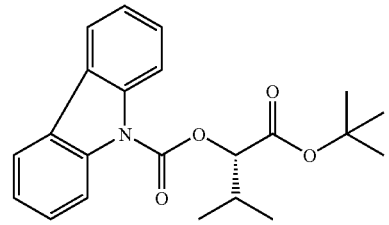

To a solution of carbazole (15.15 g) in dichloromethene (180 ml) and THF (142 ml) at 0° C. was added granulated sodium hydroxide (5.45 g) followed by tetrabutylammonium bromide (2.93 g). The resulting mixture was stirred for 30 min then a solution of chloroformate (21.41 g) in THF (81 ml) was added dropwise over 55 min. The mixture was then allowed to warm to room temperature overnight. Dichloromethane (1 L) and water (350 ml) were then added and the organic phase removed. The aqueous phase was then extracted with dichloromethane (2×250 ml) and the combined organics washed with water (200 ml), then brine (200 ml), dried (magnesium sulfate), filtered and concentrated. The residue was purified by flash chromatography (0–5% ethyl acetate/hexane) to afford the sub-title compound as a colourless oil (29.3 g): $^1$H NMR (400 MHz, CDCl$_3$) δ 1.15–1.23 (6H, m), 1.55 (9H, s), 2.52 (1H, m), 5.27 (1H, d), 7.36–7.57 (4H, m), 8.03 (2H, d), 8.47 (2H, d).

Method C:

(S)-3-methyl-2-(carbazole-carbamoyloxy)-butyric acid

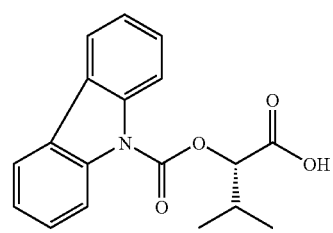

Trifluoroacetic acid (84 ml) was added dropwise to a stirred ice cold solution of (S)-3-methyl-2-(carbazole-carbamoyloxy)-butyric acid, tert-butyl ester (4.11 g) in anhydrous DCM (300 ml). The mixture was stirred at 0° C. for 2 h then at room temperature for 1 h. The mixture was concentrated under reduced pressure and then the residue dissolved in dry DCM and the solvent again removed under reduced pressure. The process was repeated several times in order to remove excess trifluoroacetic acid. This afforded the acid as a pale green gum (3.30 g): $^1$H NMR (400 MHz, CDCl$_3$) δ 1.12–1.37 (6H, m), 2.70 (1H, m), 5.47 (1H, m), 7.32–7.56 (4H, m), 8.00 (2H, d), 8.37 (2H, d).

Method D:

[3S/R, 4S/R]-5-fluoro-4-hydroxy-3-((S)-3-methyl-2-(carbazole)-carbamoyloxy-butyrylamido)-pentanoic acid, tert-butyl ester

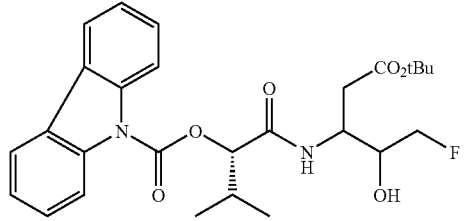

A stirred mixture of (S)-3-methyl-2-(carbazole)-carbamoyloxy-butyric acid (3.30 g), 3-amino-5-fluoro-4-hydroxy-pentanoic acid tert-butyl ester (2.42 g), HOBt (1.58 g), DMAP (1.49 g) and THF (80 ml) was cooled to 0° C. then EDC (2.24 g) was added. The mixture was allowed to warm to room temperature during 16 h then concentrated under reduced pressure. The residue was purified by flash chromatography (15–45% ethyl acetate/hexane) to afford the subtitle compound as a white foam (4.60 g): $^1$H NMR (400 MHz, CDCl$_3$) δ 1.09–1.50 (15H, m), 2.49–2.80 (3H, m), 3.20–3.62 (1H, m), 3.92–4.58 (4H, m), 5.32–5.42 (1H, d), 6.86 (1H, brm), 7.40–7.55 (4H, m), 8.02 (2H, d), 8.35 (2H, m); $^{19}$F NMR (376 MHz, CDCl$_3$) –229.6, –229.7, –230.8, –231.4.

Method E:

[3S/R]-5-Fluoro-4-oxo-3-[(S)-3-methyl-2-(carbazole-carbamoyloxy-butyrylamino]-pentanoic acid, tert-butyl ester

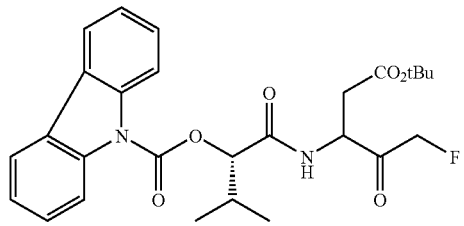

A stirred solution of [3S/R, 4S/R]-5-fluoro-4-hydroxy-3-((S)-3-methyl-2-(carbazole)-carbamoyloxy-butyrylamido)-pentanoic acid, tert-butyl ester (4.60 g) in anhydrous DCM (100 ml) was treated with 1,1,1-triacetoxy-1,1-dihydro-1,2-benziodoxol-3(1H)-one (4.68 g) at 0° C. The resulting mixture was kept at 0° C. for 2 hr, diluted with ethyl acetate, then poured into a 1:1 mixture of saturated aqueous sodium hydrogen carbonate and saturated aqueous sodium thiosulfate. The organic layer was removed and the aqueous layer re-extracted with ethyl acetate. The combined organic extracts were dried (Magnesium sulfate) and concentrated. The residue was purified by flash chromatography (10–40% ethyl acetate/hexane) to afford the subtitle compound as a white solid (3.96 g): $^1$H NMR (400 MHz, CDCl$_3$) δ 1.85 (4.5H, s), 1.94–1.31 (6H, m), 1.36 (4.5H, s), 2.59 (1H, m), 2.70–3.11 (2H, m), 4.91–5.31 (3H, m), 5.40–5.49 (1H, m), 7.25 (1H, brs), 7.42 (2H, m), 7.53 (2H, m), 8.04 (2H, m), 8.35 (2H, m); $^{19}$F NMR (376 MHz, CDCl$_3$)–232.0, –232.1.

Example 1A

[3S/R]-5-Fluoro-4-oxo-3-[(S)-3-methyl-2-(carbazole)-carbamoyloxy-butyrylamino]-pentanoic acid

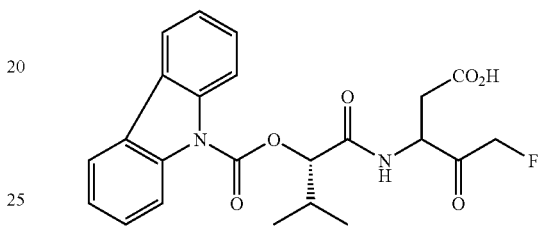

This was prepared using procedure similar to that described above in Method C. The product was isolated as a white solid (88% last step): IR (solid) 1721.2, 1695.6, 1664.9, 1449.8, 1378.1, 1198.9, 1040.1, 758.5 cm$^{-1}$; $^1$H NMR (400 MHz, d$_6$-DMSO) δ 1.10 (6H, brm), 2.41 (1H, m), 2.54–3.04 (2H, m), 4.31–4.82 (1.6H, m, CH2F), 5.10–5.41 (2.4H, m), 7.45 (2H, m), 7.57 (2H, m), 8.22 (2H, m), 8.30 (2H, m), 8.51–8.99 (1H, brm), 12.60 (1H, brs); $^{13}$C NMR (100 MHz, d$_6$-DMSO) δ 19.0, 19.1, 19.3, 30.4, 30.5, 30.6, 32.9, 34.5, 34.7, 47.3, 47.4, 52.0, 52.3, 80.4, 80.8, 83.2, 83.4, 83.4, 85.1, 85.2, 116.2, 116.3, 124.1, 125.7, 125.9, 137.9, 151.7, 151.9, 152.0, 168.8, 169.0, 169.2, 172.0, 172.1, 173.1, 173.2, 202.2, 202.4, 202.5, 202.6; $^{19}$F NMR (376 MHz, d$_6$-DMSO) –226.6 (t), –226.8 (t), –230.5 (t), –230.9(t), –232.9(t), –233.0 (t); MS (ESI +ve) 443(M+H).

Example 2

[3S/R]-5-Fluoro-4-oxo-3-[(S)-3-methyl-2-(3-chlorocarbazole)-carbamoyloxy-butyrylamino]-pentanoic acid

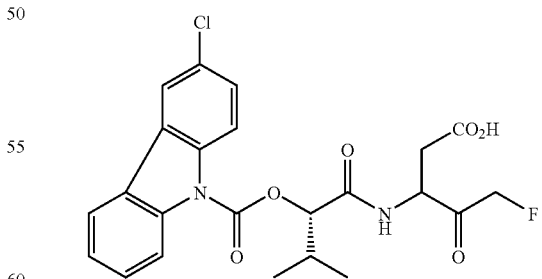

This was prepared using procedures similar to those described in methods A–E. The product was isolated as a white solid (99% last step): IR (solid) 1721.2, 1690.5, 1664.9, 1444.7, 1367.9, 1209.1, 1040.1 cm$^{-1}$; $^1$H NMR (400 MHz, d$_6$-DMSO) δ 1.02–1.13 (6H, m), 2.40 (1H, m), 2.50–2.99 (2H, m), 4.30–4.85 (1.6H, m), 5.09–5.48 (2.4H, m), 7.48 (1H, m), 7.56–7.66 (2H, m), 8.20–8.32 (3H, m), 8.39 (1H, m), 8.55–8.99 (1H, brm), 12.5 (1H, br); $^{13}$C NMR (100 MHz, d$_6$-DMSO) δ 18.1, 18.9, 19.1, 30.4, 30.5, 33.0, 34.5, 34.7, 47.4, 52.0, 52.3, 80.6, 80.9, 81.1, 83.4, 83.43, 85.1, 85.2, 103.8, 104.0, 117.0, 119.3, 121.3, 122.3, 124.3, 124.7, 127.2, 127.4, 127.9, 128.5, 136.5, 138.4, 151.5, 151.6, 151.7, 168.7, 168.9, 169.0, 169.1, 172.0, 172.1, 173.1, 173.2, 202.2, 202.4, 202.44, 202.8 (C); $^{19}$F NMR (376 MHz, d$_6$-DMSO) −226.6 (t), −226.8 (t) −230.4 (t), −230.9 (t), −231.0 (t), −232.8 (t), −232.84 (t), −232.9 (t); MS (ESI +ve) 477(M+H).

Example 3

[3S/R]-5-Fluoro-4-oxo-3-[(S)-3-methyl-2-(3,6-dichlorocarbazole)-carbamoyloxy-butyrylamino]-pentanoic acid

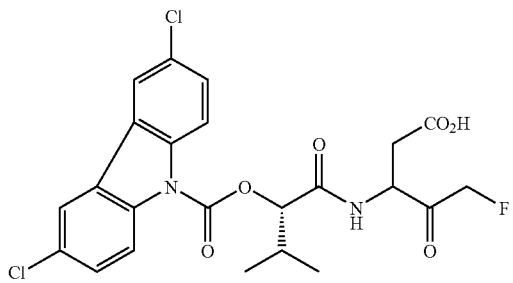

This was prepared using procedures similar to those described in methods A–E. The product was isolated as a white solid (99% last step): IR (solid) 1721.2, 1659.7, 1470.3, 1434.4, 1367.9, 1209.1, 1075.9, 1045.2 cm$^{-1}$; $^1$H NMR (400 MHz, d$_6$-DMSO) δ 0.98–1.14 (6H, m), 2.30–2.50 (1H, m), 2.50–3.01 (2H, m), 4.29–4.84 (1.5H, m), 5.09–5.41 (2.5H, m), 7.66 (2H, m), 8.19–8.29 (2H, m), 8.45 (2H, m), 8.57–8.99 (1H, brm), 12.60 (1H, br, OH); $^{13}$C NMR (100 MHz, d$_6$-DMSO) δ 15.5, 19.1, 19.2, 30.4, 30.45, 30.6, 33.0, 34.5, 34.7, 47.3, 47.5, 52.0, 52.3, 80.8, 81.1, 81.2, 83.4, 84.43, 85.1, 85.2, 117.8, 121.1, 126.3, 128.4, 128.7, 136.9, 151.2, 151.4, 168.6, 168.8, 168.9, 168.95, 172.0, 172.04, 173.1, 173.14, 202.2, 202.3, 202.4, 202.6; $^{19}$F NMR (376 MHz, d$_6$-DMSO) −226.6 (t), −226.8 (t), −230.4 (t), −230.8 (t), −232.8 (t), −232.9(t); MS (ESI +ve) 511/513 (M+H).

Example 4

[3S/R]-5-Fluoro-4-oxo-3-[(S)-3-methyl-2-(2-chlorocarbazole)-carbamoyloxy-butyrylamino]-pentanoic acid

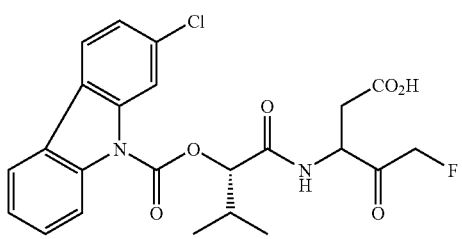

Method F:

4'-Chloro-2-nitrobiphenyl

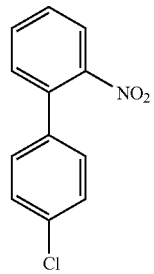

To a solution of 2-bromonitrobenzene (646 mg) in THF (17 ml) under nitrogen was added tetrakis(triphenylphosphine)palladium (0) (900 mg). The resulting mixture was stirred at room temperature for 20 min, then a solution of 4-chlorophenylboronic acid (1.0 g) in ethanol (17 ml) was added and the resulting mixture stirred at room temperature for 1 hr. 2M sodium carbonate (17 ml) was then added and the reaction heated to reflux for 2 hrs. The mixture was then allowed to cool and concentrated under reduced pressure. The residue was dissolved in ethyl acetate (100 ml) and the aqueous layer removed. The organic phase was washed with brine (20 ml), dried (magnesium sulfate), filtered and concentrated. The reside was purified by flash chromatography (0–10% ethyl acetate/hexane) to afford the sub-title compound as a yellow solid (646 mg): $^1$H NMR (400 MHz, CDCl$_3$) δ 7.24–7.31 (2H, m), 7.41–7.47 (3H, m), 7.52 (1H, m), 7.65 (1H, m), 7.90 (1H, d).

Method G:

2-Chlorocarbazole

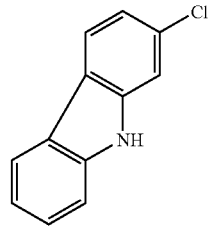

A mixture of 4'-Chloro-2-nitrobiphenyl (640 mg) and triethyl phosphite (1.9 ml) was heated at 150° C. for 3 hrs. The mixture was then allowed to cool and purified by flash chromatography (5–10% ethyl acetate/hexane) to afford the sub-title compound as a white solid (382 mg): $^1$H NMR (400 MHz, d$_6$-DMSO) δ 7.12–7.23 (2H, m), 2.40 (1H, m), 7.46–7.54 (2H, m), 8.12 (2H, d).

Example 4

[3S/R]-5-Fluoro-4-oxo-3-[(S)-3-methyl-2-(2-chlorocarbazole)-carbamoyloxy-butyrylamino]-pentanoic acid

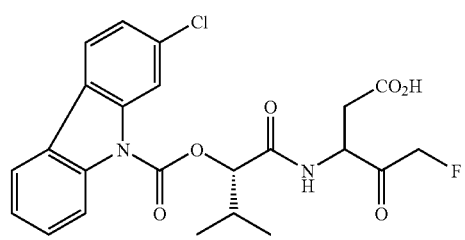

This was prepared using procedures similar to those described in methods A–E. The product was isolated as a white solid (99% last step): IR (solid) 1731.4, 1695.6, ,1664.9, 1424.2, 1367.9, 1326.9, 1193.7, 1045.2 cm$^{-1}$; $^1$H NMR (400 MHz, d$_6$-DMSO) δ 1.58–1.70 (6H, m), 2.85–3.10 (1H, m), 3.10–3.54 (2H, m), 4.85–5.39 (1.4H, m), 5.65–5.98 (2.6H, m), 7.94–8.20 (3H, m), 8.73–8.90 (4H, m), 9.10–9.56 (1H, brm), 13.2 (1H, br); $^{13}$C NMR (100 MHz, d$_6$-DMSO) δ 17.7, 17.9, 19.0, 19.1, 19.2, 30.4, 30.5, 33.0, 34.5, 34.7, 52.0, 52.3, 80.6, 80.9, 81.1, 83.4, 83.43, 85.1, 85.2, 104.0, 117.1, 121.0, 122.1, 124.2, 124.4, 124.6, 124.8, 129.0, 132.0, 138.2, 138.4, 151.6, 151.61, 168.7, 168.9, 169.0, 172.0, 172.05, 202.4, 202.42, 202.6; $^{19}$F NMR (376 MHz, d$_6$-DMSO) −225.99 (t), −226.2 (t), −229.8 (t), −230.3 (t), −232.3 (t), −232.4 (t); MS (ESI +ve) 477(M+H).

Example 5

[3S/R]-5-Fluoro-4-oxo-3-[(S)-3-methyl-2-(2,3-dichlorocarbazole)-carbamoyloxy-butyrylamino]-pentanoic acid

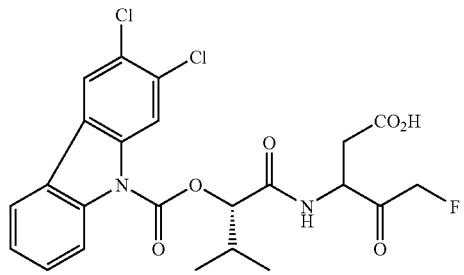

This was prepared using procedures similar to those described in methods A–E. 2,3-Dichlorocarbazole was prepared using procedures similar to those described in methods F and G. The product was isolated as a white solid (98% last step): IR (solid) 1721.2, 1659.7, 1434.4, 1367.9, 1204.0, 1188.6, 1045.2 cm$^{-1}$; $^1$H NMR (400 MHz, d$_6$-DMSO) δ 1.04–1.14 (6H, m), 2.29–2.48 (1H, m), 2.53–3.00 (2H, m), 4.30–4.84 (1.7H, m), 5.09–5.41 (2.3H, m), 7.49 (1H, m), 7.63 (1H, m), 8.20–8.33 (2H, m), 8.42–8.49 (1H, m), 8.62 (1H, m), 8.80–9.00 (1H, brm), 12.5 (1H, br); $^{13}$C NMR (100 MHz, d$_6$-DMSO) δ 17.7, 17.9, 19.0, 19.1, 30.5, 33.0, 34.5, 34.7, 47.5, 52.0, 52.3, 80.8, 81.0, 81.2, 83.4, 85.1, 85.2, 116.3, 117.9, 121.5, 122.4, 124.1, 124.6, 126.1, 126.6, 129.0, 129.7, 136.8, 138.5, 151.4, 151.45, 168.6, 168.9, 172.0, 172.03, 173.1, 202.2, 202.3, 202.4, 202.5; $^{19}$F NMR (376 MHz, d$_6$-DMSO) 226.6 (t), −226.8 (t), −230.3 (t), −230.8 (t), −232.8 (t), −232.9 (t); MS (ESI +ve) 513 (M+H).

Example 6

[3S/R]-5-Fluoro-4-oxo-3-[(S)-3-methyl-2-(2-trifluoromethyl)-carbazole-carbamoyloxy-butyrylamino]-pentanoic acid

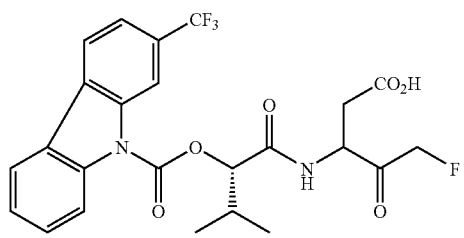

This was prepared using procedures similar to those described in methods A–E. 2-trifluoromethylcarbazole was prepared using procedures similar to those described in methods F and G. The product was isolated as a white solid (85% last step): IR (solid) 1731.4, 1695.6, 1695.7, 1434.4, 1321.8, 1198.9, 1122.1, 1065.7 cm$^{-1}$; $^1$H NMR (400 MHz, d$_6$-DMSO) δ 1.06–1.15 (6H, m), 2.42 (1H, m), 2.50–3.01 (2H, m), 4.29–4.83 (1.6H, m), 5.08–5.42 (2.4H, m), 7.53 (1H, m), 7.68 (1H, m), 7.83 (1H, m), 8.29–8.40 (2H, m), 8.48 (1H, m), 8.64 (1H, m), 8.80–9.01 (1H, m), 12.60 (1H, brs); $^{13}$C NMR (100 MHz, d$_6$-DMSO) δ 17.4, 17.6, 19.0, 19.1, 30.4, 31.0, 32.9, 34.5, 34.7, 52.0, 52.3, 80.7, 80.9, 81.1, 81.1, 83.4, 85.1, 113.3, 116.3, 120.7, 120.9, 123.6, 124.4, 126.2, 127.2, 127.5, 127.8, 128.1, 128.9, 137.2, 138.9, 151.6, 168.6, 169.0, 172.0, 202.2, 202.3, 202.4, 202.6; $^{19}$F NMR (376 MHz, d$_6$-DMSO) −60.4 (s), −226.6 (t), −226.8 (t), −229.9 (t), −230.4 (t), −231.0 (t), −232.9 (t), −233.0 (t); MS (ESI +ve) 511 (M+H).

Example 7

[3S/R]-5-Fluoro-4-oxo-3-[(S)-3-methyl-2-(2-methylcarbazole)-carbamoyloxy-butyrylamino]-pentanoic acid

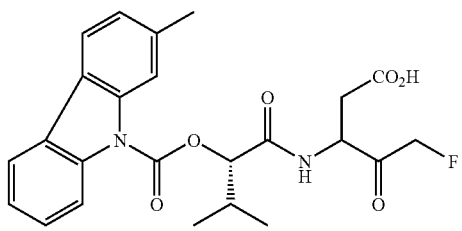

This was prepared using procedures similar to those described in methods A–E. The product was isolated as a white solid (90% last step): IR (solid) 1726.3, 1700.7, 1664.9, 1552.2, 1460.0, 1552.2, 1460.0, 1367.9, 1332.0, 1209.1, 1193.7, 1040.1 cm$^{-1}$; $^1$H NMR (400 MHz, d$_6$-DMSO) δ 1.01–1.19 (6H, m), 2.30–3.00 (6H, m), 4.29–4.85 (1.5H, m), 5.11–5.52 (2.5H, m), 7.29 (1H, m), 7.45 (1H, m), 7.55 (1H, m), 8.05–8.18 (3H, m), 8.27 (1H, m), 8.50–9.10 (1H, brm), 12.50 (1H, brs); $^{13}$C NMR (100 MHz, d$_6$-DMSO) δ 17.7, 18.0, 19.0, 19.1, 19.2, 22.2, 30.4, 30.5, 30.6, 30.6, 33.0, 34.5, 34.7, 47.4, 52.0, 52.3, 52.7, 80.3, 80.6, 80.7, 80.8, 83.2. 83.4, 83.5, 85.2, 85.2, 103.8, 104.0, 116.2, 116.3, 116.6, 120.3, 120.4, 123.4, 124.0, 125.2, 125.8, 127.3, 137.5, 137.9, 138.2, 151.7, 151.9, 151.9, 168.8, 169.0, 169.2, 169.2, 172.0, 172.1, 173.1, 173.2, 202.3, 202.4, 202.5, 202.6; $^{19}$F NMR (376 MHz, d$_6$-DMSO) −226.55 (t), −226.76 (t), −230.43 (t), −230.89 (t), −232.84 (t), −232.97 (t).

Example 8

[3S/R]-5-Fluoro-4-oxo-3-[(S)-2-(carbazole-carbamoyloxy)-butyrylamino]-pentanoic acid

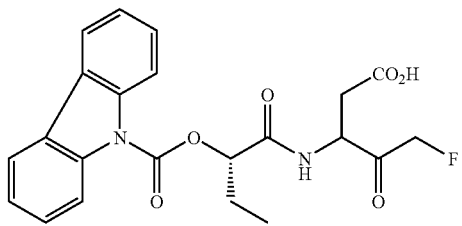

This was prepared using procedures similar to those described in methods A–E. The chloroformate was prepared from (S)-2-hydroxybutanoic acid, tert-butyl ester as described in method A. The product was isolated as a white solid (90% last step): IR (solid) 1716.1, 1654.6, 1449.8, 1372.9, 1326.9, 1204.0, 1050.4, 1029.9 cm$^{-1}$; $^1$H NMR (400 MHz, d$_6$-DMSO) δ 1.03–1.12 (3H, m), 1.96–2.15 (2H, m), 2.50–3.01 (2H, m), 4.31–4.82 (1.8H, m), 5.11–5.3 (2.2H, m), 7.45 (2H, m), 7.59 (2H, m), 8.18–8.32 (4H, m), 8.58–9.05 (1H, brm), 12.60 (1H, brs); $^{13}$C NMR (100 MHz, d$_6$-DMSO) δ 9.8, 9.9, 9.94, 24.9, 25.1, 25.2, 33.0, 34.6, 34.7, 47.4, 52.0, 52.3, 77.1, 77.3, 77.4, 77.45, 83.4, 83.5, 85.2, 85.22, 116.3, 120.6, 124.0, 125.7, 127.9, 137.9, 151.5, 151.7, 169.5, 169.8, 172.0, 172.1, 173.1, 202.3, 202.4, 202.5, 202.6; $^{19}$F NMR (376 MHz, d$_6$-DMSO) −226.6 (t), −226.8 (t), −230.4 (t), −231.0 (t), −232.9 (t), −233.0 (t).

Example 9

[3S/R]-5-Fluoro-4-oxo-3-[(S)-3,3-dimethyl-2-(carbazole-carbamoyloxy)-butyrylamino]-pentanoic acid

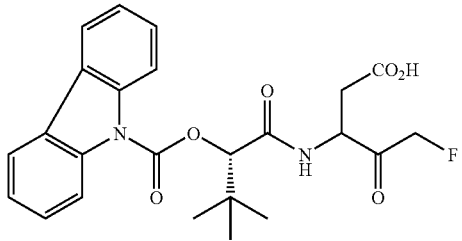

This was prepared using procedures similar to those described in methods A–E. The chloroformate was prepared from (S)-2-hydroxy-3,3-dimethylbutanoic acid, tert-butyl ester (for preparation method see *Tetrahedron. Lett.*, (1993), 7409) as described in method A. The product was isolated as a white solid (94% last step): IR (solid) 1782.7, 1721.2, 1526.6, 1444.7, 1373.0, 1332.0, 1301.3, 1198.9, 1117.0, 1040.1, 753.3 cm$^{-1}$; $^1$H NMR (400 MHz, d$_6$-DMSO) δ 1.15 (9H, s), 2.50–2.98 (2H, m), 4.29–4.88 (1.5H, m), 4.97–5.45 (2.5H, m), 7.45 (2H, m), 7.59 (2H, m), 8.23 (2H, m), 8.33 (2H, m), 8.50–8.97 (1H, brm), 12.50 (1H, brs); $^{13}$C NMR (100 MHz, d$_6$-DMSO) δ 27.3, 33.4, 34.5, 34.6, 34.7, 34.8, 35.1, 52.5, 52.9, 83.5, 83.9, 84.0, 84.1, 84.3, 85.7, 85.73, 116.7, 116.8, 121.2, 124.6, 124.64, 126.2, 128.4, 138.4, 152.2, 152.4, 152.5, 168.4, 168.7, 168.8, 168.9, 172.6, 172.65, 173.6, 202.6, 202.8, 202.9, 203.0; $^{19}$F NMR (376 MHz, d$_6$-DMSO) −226.5 (t), −226.6 (t), −230.9 (t), −231.5 (t), −232.9 (t), −233.0 (t); MS (ESI +ve) 457(M+H).

Example 10

[3S/R]-5-Fluoro-4-oxo-3-[(S)-2-(2-chlorocarbazole-carbamoyloxy-butyrylamino]-pentanoic acid

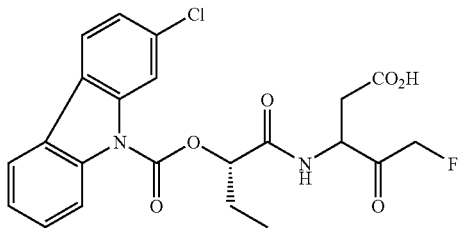

This was prepared using procedures similar to those described in methods A–E. The chloroformate was prepared from (S)-2-hydroxybutanoic acid, tert-butyl ester as described in method A. 2-Chlorocarbazole was prepared as described in methods F–G. The product was isolated as a white solid (77% last step): IR (solid) 1733.08, 1699.89, 1662.97, 1448.18, 1423.38, 1369.84, 1332.48, 1215.16, 1199.62, 1052.26, 1033.17, 764.57, 747.53, 720.08, 651.85 cm$^{-1}$; $^1$H NMR (400 MHz, d$_6$-DMSO) δ 1.06–1.10 (3H, m), 2.01–2.09 (2H, m), 2.53–2.98 (2H, m), 4.34–4.78 (1.6H, m), 5.14–5.39 (2.4H, m), 7.45–7.61 (3H, m), 8.24–8.31 (4H, m), 8.63–8.99 (1H, brm), 12.50 (1H, brs); $^{13}$C NMR (100 MHz, d$_6$-DMSO) δ 9.7, 23.7, 25.0, 31.3, 34.6, 34.8, 52.0, 52.3, 77.4, 77.6, 83.4, 85.2, 110.9, 111.6, 116.2, 116.3, 119.0, 119.4, 120.7, 120.9, 121.9, 122.1, 124.2, 124.3, 124.6, 124.8, 126.3, 128.3, 130.2, 132.0, 138.1, 138.4, 151.3, 169.6, 172.1; $^{19}$F NMR (376 MHz, d$_6$-DMSO) −226.60 (t), −226.83 (t), −230.34 (t), −231.88 (t), −232.84 (t), −232.99 (t).

Example 11

[3S/R]-5-Fluoro-4-oxo-3-[(S)-3-methyl-2-(indole)-carbamoyloxy-butyrylamino]-pentanoic acid

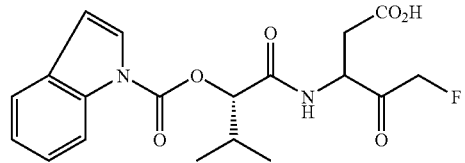

This was prepared using procedures similar to those described in methods A–E. The product was isolated as a white solid (92% last step): IR (solid) 1731.4, 1664.9, 1536.8, 1454.9, 1393.5, 1326.9, 1239.8, 1035.0 cm$^{-1}$; $^1$H NMR (400 MHz, d$_6$-DMSO) δ 1.30–1.62 (6H, m), 2.79 (1H, m), 3.00–3.48 (2H, m), 4.77–5.04 (1.6H, m), 5.42–5.88 (2.4H, m), 7.29 (1H, m), 7.70–7.90 (2H, m), 8.10–8.31 (2H, m), 8.51–8.63 (1H, m), 8.91–9.45 (1H, m), 13.0 (1H, brs); $^{13}$C NMR (100 MHz, d$_6$-DMSO) δ 15.5, 17.3, 17.6, 18.9, 19.2, 30.6, 32.9, 34.5, 34.7, 47.4, 52.0, 52.3, 65.3, 80.0, 80.3, 80.5, 83.4, 83.41, 85.1, 85.2, 104.02, 108.7, 108.71, 108.8, 114.9, 122.0, 123.5, 125.0, 126.3, 130.5, 135.0, 150.4, 168.8, 169.0, 169.1, 169.14, 172.0, 172.1, 173.1, 202.2, 202.4, 202.5, 202.6; $^{19}$F NMR (376 MHz, d$_6$-DMSO) −226.1 (t), −226.3 (t), −230.0 (t), −230.5 (t), −232.3 (t), −232.4 (t), −232.5 (t), −232.6 (t); MS (ESI +ve) 393 (M+H).

Example 12

[3S/R]-5-Fluoro-4-oxo-3-[(S)-3-methyl-2-(phonothiazine)-carbamoyloxy-butyrylamino]-pentanoic acid

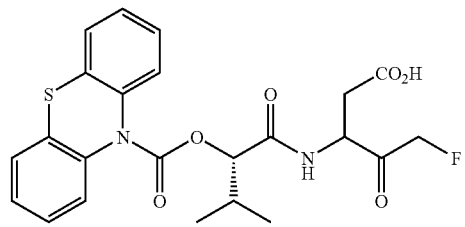

Method H:

(S)-3-methyl-2-(phonothiazine)-carbamoyloxy-butyric acid, tert-butyl ester

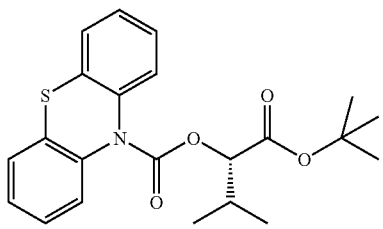

To a stirred solution of (S)-2-hydroxy-3-methylbutyric acid tert-butyl ester (for preparation method see *Tetrahedron. Lett.*, (1993), 7409) (300 mg) in THF (5 ml) at 0° C. was added sodium hydride (60% suspension in mineral oil, 72 mg). The resulting mixture was stirred for 30 minutes then phenothiazine-10-carbonylchloride (450 mg) was added and the mixture allowed to warm to ambient over 12 hrs. The reaction mixture was then diluted with ethyl acetate (15 ml) and water (3 ml). The organic phase was separated and the aqueous phase extracted with 2×5 ml of ethyl acetate. The combined organics were then washed with brine (5 ml), dried (magnesium sulfate), filtered and concentrated. The residue was purified by flash chromatography (0–10% ethyl acetate/hexane) to afford the sub-title compound as a colourless oil (528 mg): $^1$H NMR (400 MHz, CDCl$_3$) δ 0.75–0.96 (6H,m), 1.58 (9H, s), 2.20 (1H, m), 4.86 (1H, d), 7.12–7.45 (6H, m), 7.70 (2H, m).

(S)-3-methyl-2-(phonothiazine)-carbamoyloxy-butyric acid

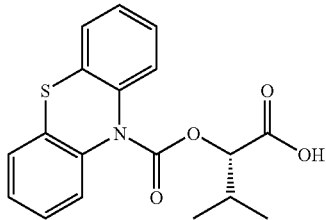

Deprotection of (S)-3-methyl-2-(phonothiazine)-carbamoyloxy-butyric acid, tert-butyl ester (528 mg) using trifluoroacetic acid as described in method C afforded the acid as a white solid(440 mg): $^1$H NMR (400 MHz, CDCl$_3$) δ 0.77–1.00 (6H, m), 2.29 (1H, m), 5.02 (1H, d), 7.15–7.48 (6H, m), 7.70 (2H, m).

Example 12

[3S/R]-5-Fluoro-4-oxo-3-[(S)-3-methyl-2-(phonothiazine)-carbamoyloxy-butyrylamino]-pentanoic acid

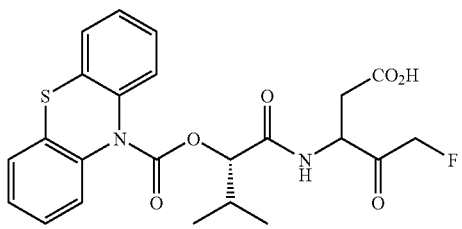

This was prepared using procedures similar to those described in methods C–E. The product was isolated as a white solid (98% last step): IR (solid) 1782.7, 1710.9, 1521.5, 1465.2, 1260.3, 1219.4, 1168.1, 1045.2, 758.5 cm$^{-1}$; $^1$H NMR (400 MHz, d$_6$-DMSO) δ 0.64–0.87 (6H, m), 1.96–2.16 (1H, m), 2.40–2.98 (2H, m), 4.50–5.42 (4H, m), 7.28 (2H, m), 7.39 (2H, m), 7.49 (2H, m), 7.68 (2H, brm), 7.88–8.91 (1H, brm), 12.61 (1H, brs); $^{13}$C NMR (100 MHz, d$_6$-DMSO) δ 16.8, 17.1, 19.0, 19.2, 30.3, 30.5, 33.0, 33.2, 34.5, 34.8, 47.3, 52.0, 52.4, 79.3, 79.6, 79.7, 83.4, 83.5, 85.1, 85.2, 103.8, 127.1, 127.2, 127.3, 127.4, 131.4, 138.0, 138.1, 152.6, 152.8, 158.82, 169.3, 169.5, 169.7, 172.0, 172.1, 172.13, 202.3, 202.4, 202.6, 202.8; $^{19}$F NMR (376 MHz, d$_6$-DMSO) −226.6 (t), −226.8 (t), −230.3 (t), −231.3 (t), −232.9 (t), −233.0 (t); MS (ESI +ve) 475(M+H).

Example 13

[3S/R]-5-Fluoro-4-oxo-3-[(S)-3-methyl-2-(2-chlorophonothiazine)-carbamoyloxy-butyrylamino]-pentanoic acid

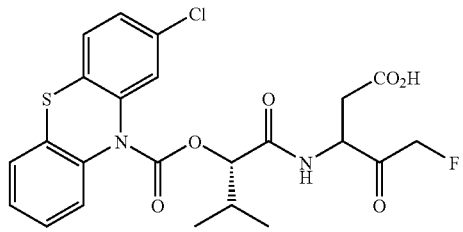

Method I:

2-Chlorophenothiazine carbamyl chloride

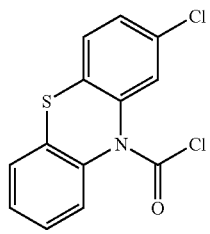

To a suspension of 2-chlorophenothiazine (2 g) in xylene (20 ml)was added diphosgene (3.4 g). The mixture was heated to 140° C. for 18 hrs. The mixture was then cooled and the xylene removed under reduced pressure. The residue was purified by flash chromatography (2–5% ethyl acetate/hexane) to afford the sub-title compound as a brown solid (2.04 g): $^1$H NMR (400 MHz, CDCl$_3$) δ 7.26–7.43 (4H, m), 7.45–7.51 (1H, m), 7.59–7.68 (2H, m).

Example 13

[3S/R]-5-Fluoro-4-oxo-3-[(S)-3-methyl-2-(2-chlorophonothiazine)-carbamoyloxy-butyrylamino]-pentanoic acid

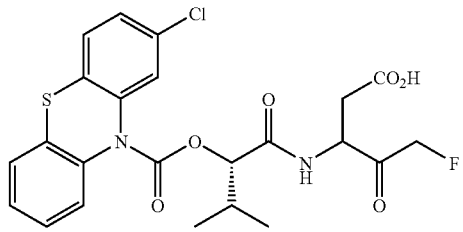

This was prepared using procedures similar to those described in methods H and C–E. The product was isolated as a white solid by reverse phase HPLC (61% last step): IR (solid) 1732, 1460, 1365, 1207 cm$^{-1}$; $^1$H NMR (400 MHz, d$_6$-DMSO) δ 0.70–0.87 (6H, m), 2.02–2.10 (1H, m), 2.58–2.90 (2H, m), 4.34–5.37 (4H, m), 7.27–7.88 (7H, m), 8.31–8.81 (1H, m); $^{13}$C NMR (100 MHz, d$_6$-DMSO) δ 16.7/16.9, 18.9/19.1, 30.3/30.3, 34.5/34.8, 52.0/52.4, 79.6/80.0, 84.2/84.3, 127.0, 127.3, 127.3, 127.6, 128.0, 129.0, 130.5, 130.9, 131.7, 137.5/137.5, 139.1/139.1, 152.3/152.5, 169.6/169.7, 172.0/172.1, 202.3/202.7 (2d, J 14.1/14.0; $^{19}$F NMR (376 MHz, d$_6$-DMSO) −226.6 (t), −226.8 (t), −233.0 (t), −233.1 (t).

Example 14

[3S/R]-5-Fluoro-4-oxo-3-[(S)-3-methyl-2-(3-chlorophonothiazine)-carbamoyloxy-butyrylamino]-pentanoic acid

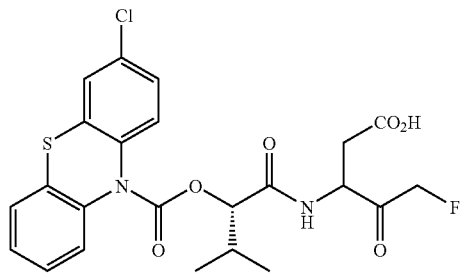

This was prepared using procedures similar to those described in methods H, I and C–E. The phenothiazine was prepared according to procedures described in *J. Chem. Soc.* (1970), 2437–2441. The product was isolated as a white solid (89% last step): IR (solid) 1717, 1527, 1469, 1350, 1322, 1217, 1042 cm$^{-1}$; $^1$H NMR (400 MHz, d$_6$-DMSO) δ 0.67–0.85 (6H, m), 2.00–2.06 (1H, m), 2.58–2.87 (2H, m), 4.33–4.86 (2.6H, m), 5.12–5.36 (1.4H, m), 7.27–7.30 (1H, m), 7.38–7.51 (3H, m), 7.63–7.68 (3H, m), 8.24–8.82 (1H, m); $^{13}$C NMR (100 MHz, d$_6$-DMSO) δ 17.3/17.6 (CH3), 19.4/19.5 (CH3), 30.8/30.8, 35.0/35.3, 52.5/52.9, 80.0/80.1, 84.7/84.8, 127.2, 127.3, 127.6, 127.9, 128.6, 130.7, 131.2, 133.7, 136.9/137.0, 137.8/137.8, 153.0/153.2, 170.1/170.2, 172.5/172.6, 202.9/203.2; $^{19}$F NMR (376 MHz, d$_6$-DMSO) −226.7 (br), −226.9 (br), −233.0 (t); MS (ESI +ve) 509/511(M+H).

Example 15

[3S/R]-5-Fluoro-4-oxo-3-[(S)-3-methyl-2-(3,7-dichlorophonothiazine)-carbamoyloxy-butyrylamino]-pentanoic acid

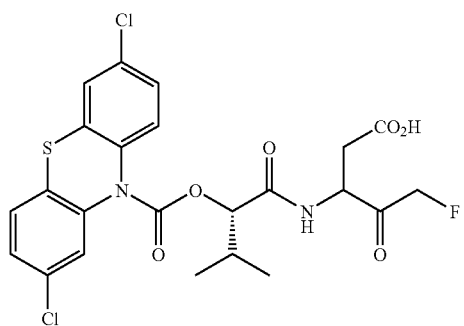

This was prepared using procedures similar to those described in methods H, I and C–E. The phenothiazine was prepared according to procedures described in *J. Chem. Soc.* (1970), 2437–2441. The product was isolated as a white solid by reverse phase HPLC (76% last step): IR (solid) 1793, 1721, 1521, 1465, 1317, 1214, 1086, 1044 cm$^{-1}$; $^1$H NMR (400 MHz, d$_6$-DMSO) δ 0.71–0.76 (3H, m), 0.84–0.88 (3H, m), 2.05–2.12 (1H, m), 2.58–2.92 (2H, m), 4.31–4.87 (2.5H, m), 5.09–5.36 (1.5H, m), 7.47–7.56 (2H, m), 7.67–7.71 (2H, m), 7.72–7.81 (1H, m), 8.39–8.87 (1H, m); $^{13}$C NMR (100 MHz, d$_6$-DMSO) δ 16.7/16.7/17.0, 19.0/19.1/19.2/19.3, 30.3/30.3/30.4, 34.5/34.8, 52.0/52.4, 79.8/80.1, 84.2/84.3, 127.3, 127.4, 127.7, 128.5, 129.2, 129.7, 131.4/131.4, 132.0, 133.1/133.2, 136.4/136.5, 138.8/138.9, 152.2/152.3, 169.5/169.6, 172.0/172.1, 202.4/202.5; $^{19}$F NMR (376 MHz, d$_6$-DMSO) −226.5 (br), −226.8 (t), −232.9 (t), −233.0 (br).

Example 16

[3S/R]-5-Fluoro-4-oxo-3-[(S)-3-methyl-2-(3,4-dichlorophonothiazine)-carbamoyloxy-butyrylamino]-pentanoic acid

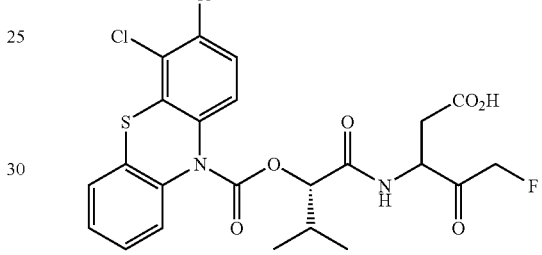

This was prepared using procedures similar to those described in methods H, I and C–E. The phenothiazine was prepared according to procedures described in *J. Chem. Soc.* (1970), 2437–2441. The product was isolated as a white solid by reverse phase HPLC (58% last step): IR (solid) 1736, 1436, 1365, 1222, 1050 cm$^{-1}$; $^1$H NMR (400 MHz, d$_6$-DMSO) δ 0.66–0.85 (6H, m), 2.00–2.08 (1H, m), 2.57–2.93 (2H, m), 4.30–5.35 (4H, m), 7.31–7.71 (6H, m), 8.27–8.83 (1H, m); $^{13}$C NMR (100 MHz, d$_6$-DMSO) δ 16.8/17.1, 19.0/19.1, 30.3, 34.5/34.8, 52.0/52.4, 79.7/80.0, 84.2/84.3, 179.2/178.6, 127.1, 127.3, 127.5, 128.2, 128.5, 128.5, 129.6, 130.0, 133.7, 137.3/137.3, 137.6/137.6, 152.5, 169.5/169.5, 172.0/172.1, 202.3; $^{19}$F NMR (376 MHz, d$_6$-DMSO) −226.6 (t), −226.8 (t), −232.9 (t).

Example 17

[3S/R]-5-Fluoro-4-oxo-3-[(S)-3-methyl-2-(9,10-Dihydrophenanthridine)-carbamoyloxy-butyrylamino]-pentanoic acid

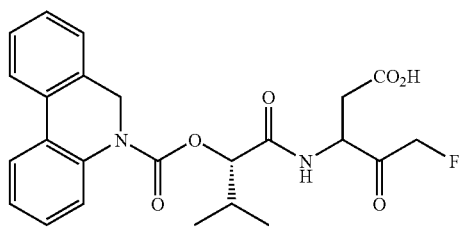

This was prepared using procedures similar to those described in methods H, I and C–E. 9,10-Dihydrophenanthridine was prepared as described in *J. Chem. Soc.* (1951), 3207–3211. The product was isolated as a white solid by reverse phase HPLC(56% last step): IR (solid) 1732, 1365, 1226, 1212, 1203 cm$^{-1}$; $^1$H NMR (400 MHz, d$_6$-DMSO) δ 0.84 (6H, m), 2.05 (1H, m), 2.55–2.90 (2H, m), 4.28–5.36 (6H, m), 7.26–7.43 (5H, m), 7.75–7.77 (1H, m), 7.89–7.91 (2H, m), 8.24–8.81 (1H, m); $^{13}$C NMR (100 MHz, d$_6$-DMSO) δ 17.1/17.4, 18.9/19.0, 30.3/30.4, 34.4/34.8, 46.9, 51.9/52.4, 79.0/79.4, 84.2/84.3, 123.8, 124.3, 125.1, 125.7, 126.2, 128.0, 128.2, 128.3, 128.5, 131.5, 134.1, 136.9, 153.1, 170.0/170.1, 172.0/172.1, 202.4/202.8; $^{19}$F NMR (376 MHz, d$_6$-DMSO) −226.7 (br), −226.9 (br), −233.1 (t); MS (ESI −ve) 455(M−H).

Example 18

Dibenzo[b,f]azepine-5-carboxylic acid 1-(1-carboxymethyl-3-fluoro-2-oxo-propylcarbamoyl)-2-methyl-propyl ester

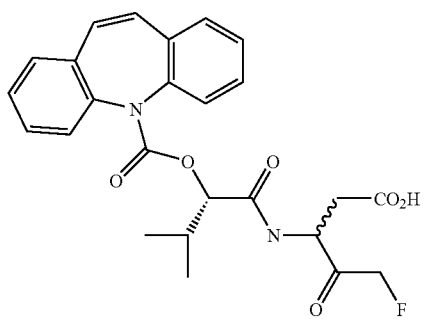

This was prepared using procedures similar to those described in methods H, I and C–E. The product was isolated as a white solid (100% last step): IR (solid) 1791.2, 1714.9, 1683.4, 1525.6, 1492.6, 1370.1, 1325.6, 1229.3, 1212.5, 1053.4, 1032.7, 798.4 cm$^{-1}$; $^1$H NMR (400 MHz, d$_6$-DMSO) δ 0.50+0.68 (6H, 2×m), 1.90 (1H, m), 2.54–2.93 (2H, m), 4.20–5.44 (4H, m), 7.02 (2H, s), 7.30–7.80 (8H, m); $^{13}$C NMR (100 MHz, d$_6$-DMSO) δ 18.73, 19.17, 30.34, 34.56, 52.18, 84.37, 127.92, 128.61, 128.69, 129.63, 130.83, 134.40, 153.90, 169.64, 172.23, 202.29, 202,43, 202.63 202.76; $^{19}$F NMR (376 MHz, d$_6$-DMSO) −226.83 (t), −226.87 (t), −232.93 (t), −233.07 (t), −233.10 (t), −233.32 (t); MS (ESI +ve) 469(M+H).

Example 19

10,11-Dihydro-dibenzo[b,f]azepine-5-carboxylic acid 1-(1-carboxymethyl-3-fluoro-2-oxo-propylcarbamoyl)-2-methyl-propyl ester

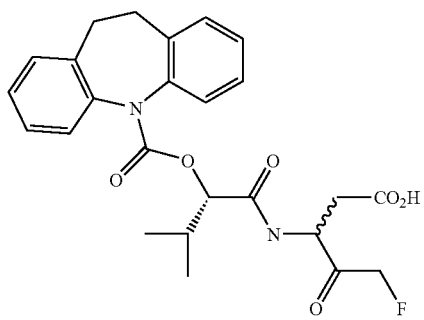

This was prepared using procedures similar to those described in methods H, I and C–E. The product was isolated as a white solid (100% last step): IR (solid) 1796.9, 1683.9, 1521.8, 1491.5, 1368.3, 1324.8, 1278.6, 1213.4, 1201.9, 1108.0, 1056.4, 931.1, 776.5, 746.7 cm$^{-1}$; $^1$H NMR (400 MHz, d$_6$-DMSO) δ 0.50–0.95 (6H, m), 1.90 (1H, m), 2.55–3.00 (2H, m), 4.20–5.30 (8H, m), 7.10–7.50 (8H, m); $^{13}$C NMR (100 MHz, d$_6$-DMSO) δ 15.24, 16.79, 39.44, 52.43, 78.36, 84.34, 126.80, 1227.89, 128.43, 130.29, 136.29, 154.09, 169.58, 170.03, 172.19, 173.12, 202.28, 202.42; $^{19}$F NMR (376 MHz, d$_6$-DMSO) −226.76 (t), −233.01 (t), −233.11 (t), −233.38 (t); MS (ESI +ve) 471(M+H).

Example 20

[3S/R]-5-Fluoro-4-oxo-3-((S)-2,3-dihydroindole-1-carbamoyloxy-3-methyl-butyrylamino)-pentanoic acid

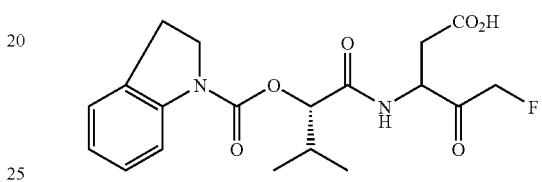

Method J:

(S)-2-(imidazolecarbamoyloxy)-3-methylbutyric acid, benzyl ester

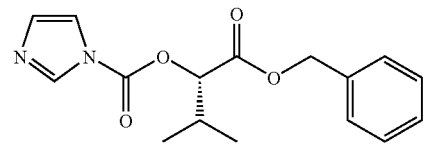

To a stirred solution of (S)-2-hydroxy-3-methylbutyric acid benzyl ester (for preparation see *J. Med. Chem.*, (1996), 39, 982, 1.5 g) in THF (20 ml) was added carbonyldiimidazole (1.17 g) and the resulting mixture stirred at room temperature for 12 h. Reaction mixture was concentrated under reduced pressure and the residue re-dissolved in ethyl acetate (30 ml). The solution was washed with 1% phosphoric acid (2×10 ml, then brine (10 ml), dried (magnesium sulfate), filtered and concentrated to afford the sub-title compound as a colourless oil (1.89 g): $^1$H NMR (400 MHz, CDCl$_3$) δ 1.02 (3H, d), 1.11 (3H, d), 2.47 (1H, m), 5.15 (1H, d), 5.18–5.32 (2H, m), 7.11 (1H, s), 7.18–7.60 (6H, m), 8.20 (1H, m).

Method K:

(S)-(2,3-dihydroindole-1-carbamoyloxy)-3-methylbutyric acid, benzyl ester

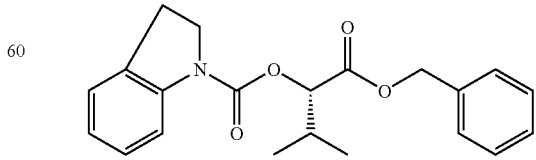

To a stirred solution of (S)-2-(imidazolecarbamoyloxy)-3-methylbutyric acid, benzyl ester (355 mg) in THF (7 ml)

at 0° C. was added methyl trifluoromethanesulfonate (0.13 ml). The resulting solution was stirred for 30 min. Indoline (280 mg) was then added and the mixture allowed to warm to room temperature over 12 hrs. Reaction mixture was concentrated under reduced pressure and the residue re-dissolved in ethyl acetate (30 ml). The solution was washed with saturated sodium bicarbonate solution (5 ml) then 1M hydrochloric acid (2×5 ml), then brine (5 ml), dried (magnesium sulfate), filtered and concentrated. The residue was purified by flash chromatography (5–7% ethyl acetate/hexane) to afford the sub-title compound as a colourless oil (342 mg): $^1$H NMR (400 MHz, CDCl$_3$) δ 0.86–1.18 (6H, m), 2.35 (1H, m), 3.08–3.25 (2H, m), 4.05–4.25 (2H, m), 4.95–5.32 (3H, m), 6.95–7.91 (9H, m).

Method L:

(S)-(2,3-dihydroindole-1-carbamoyloxy)-3-methylbutyric acid

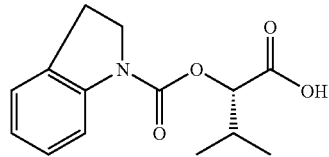

A stirred solution of (S)-(2,3-dihydroindole-1-carbamoyloxy)-3-methylbutyric acid, benzyl ester (342 mg) in methanol (25 ml) was added 10% palladium on carbon (80 mg). The mixture was hydrogenated at room temperature for 2 hrs. The mixture was then filtered through celite and the filtrate concentrated to afford the sub-title compound as a colourless oil (255 mg): $^1$H NMR (400 MHz, CDCl$_3$) δ 0.95–1.21 (6H, m), 2.40 (1H, m), 3.20 (2H, m), 4.01–4.25 (2H, m), 4.95–5.15 (1H, m), 6.97–7.99 (4H, m).

Example 20

[3S/R]-5-Fluoro-4-oxo-3-((S)-2,3-dihydroindole-1-carbamoyloxy-3-methyl-butyrylamino)-pentanoic acid

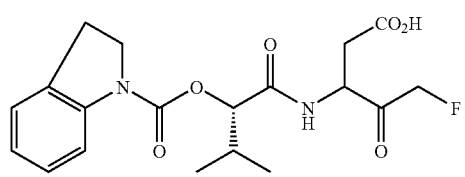

This was prepared using procedures similar to those described in methods C–E. The product was isolated as a white solid (94% last step): IR (solid) 1680.2, 1485.6, 1413.9, 1137.4, 1050.4, 758.5 cm$^{-1}$; $^1$H NMR (400 MHz, d$_6$-DMSO) δ 0.95 (6H, brm), 2.17 (1H, brm), 2.50–2.94 (2H, m), 3.12 (2H, brm), 3.84–4.23 (2H, brm), 4.27–5.39 (4H, m), 6.98 (1H, m), 7.22 (2H, m), 7.67 (1H, brm), 7.78–8.30 (1H, brm), 12.50 (1H, brs); $^{13}$C NMR (100 MHz, d$_6$-DMSO) δ 17.2, 19.0, 19.2, 27.3, 30.4, 30.6, 32.9, 34.5, 34.6, 47.2, 47.35, 52.0, 52.2, 78.3, 83.4, 85.1, 104.0, 114.2, 123.0, 125.4, 127.5, 131.7, 170.0, 172.07, 172.1, 173.2, 173.25, 202.3, 202.5, 202.6; $^{19}$F NMR (376 MHz, d$_6$-DMSO) −226.7 (t), −226.8 (t), −233.1 (t), −233.3 (t); MS (ESI +ve) 395(M+H).

Example 21

[3S/R]-5-Fluoro-4-oxo-3-[(S)-3-methyl-2-(carbazole)-carbamoyloxy-butyrylamino]-pentanoic acid, diethylamide

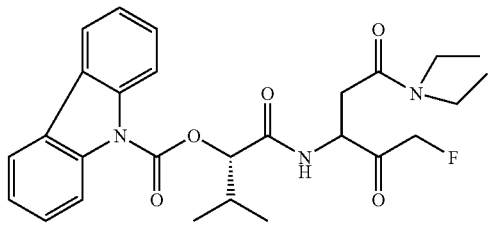

Method M:

To a stirred solution of acid (Example 1; prepared as described in methods A–E) (100 mg) in THF (2 ml) at 0° C. was added diethylamine (16 mg) in THF (0.5 ml) followed by 1-(3-dimetlaminopropyl)-3-(ethylcarbodiimide hydrochloride, EDC) (48 mg). The mixture was then warmed to room temperature over 12 hrs. Solvent was removed under reduced pressure and the residue purified by flash chromatography (50–60% ethyl acetate/hexane) to afford the amide as a white solid (54 mg); $^1$H NMR (400 MHz, CDCl$_3$) δ 0.69–1.38 (12H, m), 2.42–3.37 (7H, m), 4.85–4.92 (1H, m), 5.01–5.55 (3H, m), 7.31–7.70 (5H, m), 7.90–8.05 (2H, m), 8.25–8.42 (2H, m); $^{19}$F NMR (376 MHz, CDCl$_3$) −232.6 (t), −232.8 (t); MS (ESI +ve) 498(M+H).

Example 22

[3S/R]-5-Fluoro-4-oxo-3-[(S)-3-methyl-2-(carbazole)-carbamoyloxy-butyrylamino]-pentanoic acid, ethyl amide

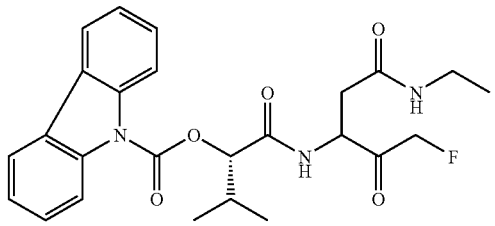

This was prepared using procedures similar to those described in method M. The product was isolated as a white solid (62%): $^1$H NMR (400 MHz, CDCl$_3$) δ 0.96–1.31 (9H, m), 2.21–2.45 (1H, m), 2.48–2.80 (2H, m), 3.15–3.48 (2H, m), 4.23–4.76 (3H, m), 5.05–5.42 (1H, m), 6.42–6.84 (1H, m), 7.38–7.60 (4H, m), 7.95–8.09 (2H, m), 8.20–8.41 (2H, m); $^{19}$F NMR (376 MHz, CDCl$_3$) −223.8 (t), −224.5 (t), −226.5 (t), −227.1 (t), −231.9 (t), −232 (t); MS (ESI +ve) 452(M+H$_2$O).

Example 23

[3S/R]-5-Fluoro-4-oxo-3-[(S)-3-methyl-2-(carbazole)-carbamoyloxy-butyrylamino]-pentanoic acid, piperazine amide

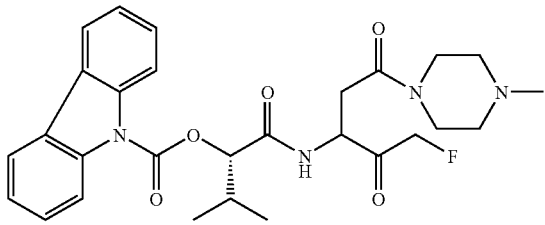

This was prepared using procedures similar to those described in method M. The product was isolated as a white solid (78%): $^1$H NMR (400 MHz, CDCl$_3$) δ 1.10–1.35 (6H, m), 1.80–3.55 (14H, m), 4.82–4.98 (1H, m), 5.00–5.45 (3H, m), 7.38–7.60 (5H, m), 7.95–8.08 (2H, m), 8.27–8.45 (2H, m); $^{19}$F NMR (376 MHz, CDCl$_3$) −232.5 (t), −232.7 (t); ); MS (ESI +ve) 525(M+H).

Example 24

[3S/R]-5-Fluoro-4-oxo-3-[(S)-3-methyl-2-(carbazole)-carbamoyloxy-butyrylamino]-pentanoic acid, N, N-dimethylaminoethyl amide

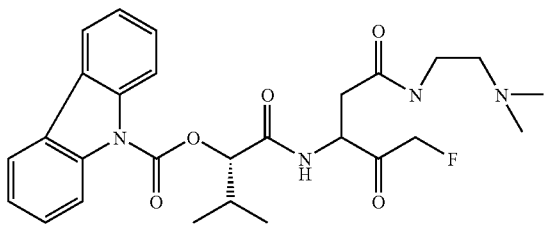

This was prepared using procedures similar to those described in method M. The product was isolated as a white solid (49%): $^1$H NMR (400 MHz, CDCl$_3$) δ 1.14–1.31 (6H, m), 1.88–3.04 (13H, m), 3.88–4.41 (3H, m), 4.57–4.74 (1H, m), 5.33–5.61 (1H, m), 6.86–7.12 (1H, m), 7.33–7.56 (4H, m), 8.01–8.05 (2H, m), 8.27–8.41 (2H, m); $^{19}$F NMR (376 MHz, CDCl$_3$) −222.4 (t), −222.5 (t); MS (ESI +ve) 513(M+H).

Example 25

[3S/R]-5-Fluoro-4-oxo-3-[(S)-3-methyl-2-(carbazole)-carbamoyloxy-butyrylamino]-pentanoamide

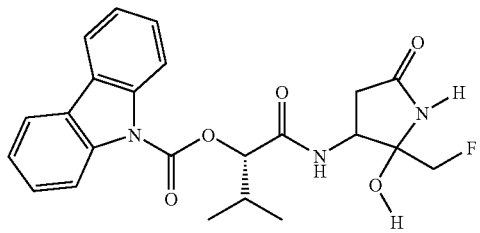

Method N:

To a stirred solution of [3S/R]-5-Fluoro-4-oxo-3-[(S)-3-methyl-2-(carbazole-carbamoyloxy-butyrylamino]-pentanoic acid from Example 1 (150 mg) in dichloromethane (1.5 ml) and dimethylformamide (0.075 ml) was added carbonyldiimidazole (66 mg). The mixture was stirred for 2 hrs then cooled to 0° C. whilst ammonia was bubbled through. The mixture was diluted with ethyl acetate/10% potassium hydrogen sulfate solution. The organic phase was removed and the aqueous extracted with ethyl acetate. The combined organics were dried over magnesium sulfate, filtered and concentrated. The residue was purified by flash chromatography (5% methanol/dichloromethane) to afford the amide as a white solid (80 mg); $^1$H NMR (400 MHz, CDCl$_3$) 1.10–1.28 (6H, m), 2.12–2.75 (3H, m), 4.10–4.85 (4H, m), 5.29 (1H, m), 6.36,6.55, 6.78,6.98 (1H, 4×s), 7.17 (1H, m), 7.42 (2H, m), 7.50 (2H, m), 7.99 (2H, m), 8.29 (2H, m); $^{19}$F NMR (376 MHz, CDCl$_3$) −225.47 (t), −226.00 (t), −227.33 (t), −227.50 (t), −228.43 (t); MS (ESI +ve) 424 (M–H$_2$O+H).

Example 26

[3S/R]-5-Fluoro-4-oxo-3-[(S)-3-methyl-2-(carbazole)-carbamoyloxy-butyrylamino]-pentanoic acid, cyclohexy ester

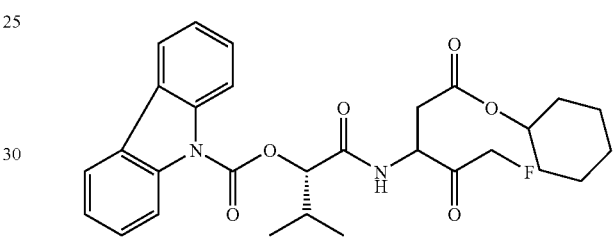

This was prepared using procedures similar to those described in method M. The product was isolated as a white solid (37%): $^1$H NMR (400 MHz, CDCl$_3$) δ 0.90–1.80 (16H, m), 2.59 (1H, m), 2.75–3.15 (2H, m), 4.40 (0.5H, m), 4.64 (0.5H, m), 4.95–5.45 (4H, m), 7.25 (1H, m), 7.42 (2H, m), 7.52 (2H, m), 8.05 (2H, m), 8.36 (2H, m); $^{19}$F NMR (376 MHz, CDCl$_3$) −231.95 (t), −232.08 (t).

Example 27

[3S/R]-5-Fluoro-4-oxo-3-[(S)-3-methyl-2-(carbazole)-carbamoyloxy-butyrylamino]-pentanoic acid, n-propyl ester

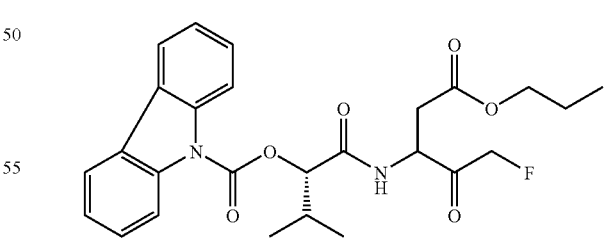

This was prepared using procedures similar to those described in method M. The product was isolated as a white solid (82%): $^1$H NMR (400 MHz, CDCl$_3$) δ 0.80 (3H, m), 1.13–1.36 (6H, m), 1.42 (1H, m), 1.58 (1H, m), 2.60 (1H, m), 2.80–3.08 (2H, m), 3.70 (1H, m), 3.98 (1H, m), 4.92–5.50 (4H, m), 7.21 (1H, m), 7.40 (2H, m), 7.50 (2H, m), 8.00 (2H,m), 8.32 (2H, m); $^{19}$F NMR (376 MHz, CDCl$_3$) −232.00 (t), −232.01 (t); MS (ESI +ve) 485 (M+H).

Example 28

[3S/R]-5-Fluoro-4-oxo-3-[(S)-3-methyl-2-(carbazole)-carbamoyloxy-butyrylamino]-pentanoic acid, isopropyl ester

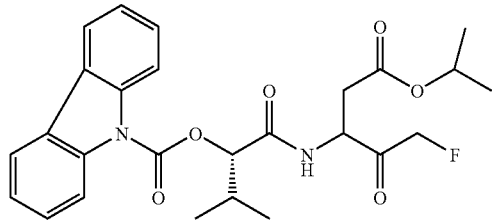

This was prepared using procedures similar to those described in Method M. The product was isolated as a white solid (7%): $^1$H NMR (400 MHz, CDCl$_3$) δ 0.90–1.33 (12H, m), 2.55 (1H, m), 2.78–3.15 (2H, m), 4.80–5.50 (5H, m), 7.25 (1H, br s), 7.43 (2H, m), 7.55 (2H, m), 8.05 (2H, m), 8.36 (2H, m); $^{19}$F NMR (376 MHz CDCl$_3$) −232.00 (t), −232.03 (t).

Example 29

[3S/R]-5-Fluoro-4-oxo-3-[(S)-3-methyl-2-(carbazole)-carbamoyloxy-butyrylamino]-pentanoic acid, methyl ester

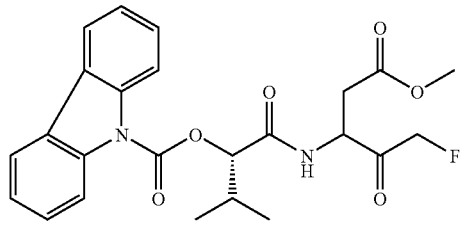

This was prepared using procedures similar to those described in method M. The product was isolated as a white solid (81%): δ $^1$H NMR (400 MHz CDCl$_3$) 1.20 (6H, m), 2.58 (1H, m), 2.80–3.05 (2H, m), 3.42, 3.61 (3H, 2×s), 4.98–5.26 (3H, m), 5.41 (1H, m), 7.20 (1H, br s), 7.45 (2H, m), 7.55 (2H, m), 8.04 (2H, m), 8.35 (2H, m); $^{19}$F NMR (376 MHz CDCl$_3$) −231.99 (t), −232.00 (t); MS (ESI +ve) 457 (M+H).

Example 30

[3S/R]-5-Fluoro-4-oxo-3-[(S)-3-methyl-2-(carbazole)-carbamoyloxy-butyrylamino]-pentanoic acid, cholesterol ester This was prepared using procedures similar to those described in method N, using carbonyldiimidazole as the coupling reagentcccs. The product was isolated as a white solid (12%): $^1$H NMR (400 MHz, CDCl$_3$) δ 0.65–2.35 (47H, m), 2.58 (1H, m), 2.75–3.15 (2H, m), 4.25 (0.5H, m), 4.48 (0.5H, m), 4.97–5.46 (5H, m), 7.30 (1H, m), 7.44 (2H, m), 7.58 (2H, m), 8.05 (2H, m), 8.33 (1H, m); $^{19}$F NMR (376 MHz CDCl$_3$) −231.91 (t), −232.03 (t). The corresponding ketal was also isolated as a white solid (21%): $^1$H NMR (400 MHz CDCl$_3$) δ 0.65–2.10 (48H, m), 2.35–3.15 (2H, 3×m), 3.42–3.69 (1H, m), 4.10–4.96 (4H, m), 5.15–5.65 (2H, m), 6.78 (1H, m), 7.45 (2H, m), 7.57 (2H, m), 8.05 (2H, m), 8.34 (2H, m); $^{19}$F NMR (376 MHz CDCl$_3$) −230.57 (t), −230.67 (t).

Testing Methods

Enzyme Assays

The assays for caspase inhibition are based on the cleavage of a fluorogenic substrate by recombinant, purified human Caspases-1, -3, -7 or -8. The assays are run in essentially the same way as those reported by Garcia-Calvo et al. (J. Biol. Chem. 273 (1998), 32608–32613), using a substrate specific for each enzyme. The substrate for Caspase-1 is Acetyl-Tyr-Val-Ala-Asp-amino-4-methylcoumarin. The substrate for Caspases-3, -7 and -8 is Acetyl-Asp-Glu-Val-Asp-amino-4-methylcoumarin.

The observed rate of enzyme inactivation at a particular inhibitor concentration, $k_{obs}$, is computed by direct fits of the data to the equation derived by Thornberry et al. (Biochemistry 33 (1994), 3943–3939) using a nonlinear least-squares analysis computer program (PRISM 2.0; GraphPad software). To obtain the second order rate constant, $k_{inact}$, $k_{obs}$ values are plotted against their respective inhibitor concentrations and $k_{inact}$ values are subsequently calculated by computerized linear regression. Many of the present compounds that were tested had, against caspase-1, $k_{inact}$ values between 25,000 and 1,500,000 $M^{-1}s^{-1}$; against caspase-3, $k_{inact}$ values between 9,000 and 1,500,000 $M^{-1}s^{-1}$; against caspase-8, $k_{inact}$ values between 10,000 and 700,000 $M^{-1}s^{-1}$.

Inhibition of IL-1β Secretion from Mixed Population of Peripheral Blood Mononuclear Cells (PBMC)

Processing of pre-IL-1β by caspase-1 may be measured in cell culture using a variety of cell sources. Human PBMC obtained from healthy donors provides a mixed population of lymphocyte and mononuclear cells that produce a spectrum of interleukins and cytokines in response to many classes of physiological stimulators.

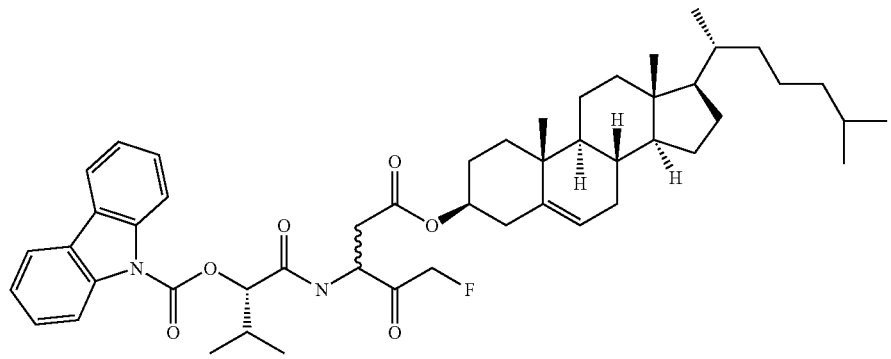

Experimental Procedure

The test compound is dissolved in dimethyl sulfoxide (DMSO,Sigma #D-2650) to give a 100 mM stock solution. This is diluted in complete medium consisting of RPMI containing 10% heat inactivated FCS (Gibco BRL #10099–141), 2 mM L-Glutamine (Sigma, #G-7513), 100 U penicillin and 100 µg/ml streptomycin (Sigma #P-7539). The final concentration range of test compound is from 100 µM down to 6 nM over eight dilution steps. The highest concentration of test compound is equivalent to 0.1% DMSO in the assay.

Human PBMC are isolated from Buffy Coats obtained from the blood bank using centrifugation on Ficoll-Paque leukocyte separation medium (Amersham, #17-1440-02) and the cellular assay is performed in a sterile 96 well flat-bottomed plate (Nunc). Each well contains 100 µl of the cell suspension, $1 \times 10^5$ cells, 50 µl of compound dilutions and 50 µl of LPS (Sigma #L-3012) at 50 ng/ml final concentration. Controls consist of cells +/−LPS stimulation and a serial dilution of DMSO diluted in the same way as compound. The plates are incubated for 16–18 h at 37° C. in 5% $CO_2$ & 95% humidity atmosphere.

After 16–18 h the supernatants are harvested after centrifuging the plates at 100×g at 18° C. for 15 min and assayed for their IL-1β content. Measurement of mature IL-1β in the supernatant is performed using the Quantikine kits (R&D Systems) according to manufacturer's instructions. Mature IL-1β levels of about 600–1500 pg/ml are observed for PBMCs in positive control wells.

The inhibitory potency of the compounds may be represented by an $IC_{50}$ value, which is the concentration of inhibitor at which 50% of the mature IL-1β is detected in the supernatant as compared to the positive controls. Table 5 shows inhibition of IL-1β secretion from peripheral blood mononuclear cells for selected compounds of this invention as determined by the above methods.

Selected compounds have been tested in this assay and shown to inhibit IL-1β release with $IC_{50}$ values between 0.04 µM and 20 µM.

Anti-Fas Induced Apoptosis Assay

Cellular apoptosis may be induced by the binding of Fas ligand (FasL) to its receptor, CD95 (Fas). CD95 is one of a family of related receptors, known as death receptors, which can trigger apoptosis in cells via activation of the caspase enzyme cascade. The process is initiated by the binding of the adapter molecule FADD/MORT-1 to the cytoplasmic domain of the CD-95 receptor-ligand complex. Caspase-8 then binds FADD and becomes activated, initiating a cascade of events that involve the activation of downstream caspases and subsequent cellular apoptosis. Apoptosis can also be induced in cells expressing CD95 eg the Jurkat E6.1 T cell lymphoma cell line, using an antibody, rather than FasL, to crosslink the cell surface CD95. Anti-Fas-induced apoptosis is also triggered via the activation of caspase-8. This provides the basis of a cell based assay to screen compounds for inhibition of the caspase-8-mediated apoptotic pathway.

Experimental Procedure

Jurkat E6.1 cells are cultured in complete medium consisting of RPMI-1640 (Sigma No)+10% foetal calf serum (Gibco BRL No.10099-141)+2 mM L-glutamine (Sigma No. G-7513). The cells are harvested in log phase of growth. 100 ml of cells at $5-8 \times 10^5$ cells/ml are transferred to sterile 50 ml Falcon centrifuge tubes and centrifuged for 5 minutes at 100×g at room temperature. The supernatant is removed and the combined cell pellets resuspended in 25 ml of complete medium. The cells are counted and the density adjusted to $2 \times 10^6$ cells/ml with complete medium.

The test compound is dissolved in dimethyl sulfoxide (DMSO)(Sigma No. D-2650) to give a 100 mM stock solution. This is diluted to 400 µM in complete medium, then serially diluted in a 96-well plate prior to addition to the cell assay plate.

100 µl of the cell suspension ($2 \times 10^6$ cells) is added to each well of a sterile 96-well round-bottomed cluster plate (Costar No. 3790). 50 µl of compound solution at the appropriate dilution and 50 µl of anti-Fas antibody, clone CH-11 (Kamiya No.MC-060) at a final concentration of 10 ng/ml, are added to the wells. Control wells are set up minus antibody and minus compound but with a serial dilution of DMSO as vehicle control. The plates are incubated for 16–18 hrs at 37° C. in 5% $CO_2$ and 95% humidity.

Apoptosis of the cells is measured by the quantitation of DNA fragmentation using a 'Cell Death Detection Assay' from Boehringer-Mannheim, No. 1544 675. After incubation for 16–18 hrs the assay plates are centrifuged at 100×g at room temperature for 5 minutes. 150 µl of the supernatant are removed and replaced by 150 µl of fresh complete medium. The cells are then harvested and 200 µl of the lysis buffer supplied in the assay kit are added to each well. The cells are triturated to ensure complete lysis and incubated for 30 minutes at 4° C. The plates are then centrifuged at 1900×g for 10 minutes and the supernatants diluted 1:20 in the incubation buffer provided. 100 µl of this solution is then assayed according to the manufacturer's instructions supplied with the kit. $OD_{405}$ nm is measured 20 minutes after addition of the final substrate in a SPECTRAmax Plus plate reader (Molecular Devices). OD405 nm is plotted versus compound concentration and the IC50 values for the compounds are calculated using the curve-fitting program SOFTmax Pro (Molecular Devices) using the four parameter fit option.

Selected compounds have been tested in this assay and shown to inhibit Fas-induced apoptosis of Jurkat cells with $IC_{50}$ values between 0.001 µM and 0.15 µM.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

The invention claimed is:

1. A compound of formula I:

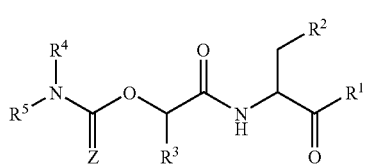

wherein:

Z is oxygen or sulfur;

$R^1$ is hydrogen, —$CHN_2$, —R, —$CH_2OR$, —$CH_2SR$, or —$CH_2Y$;

R is a $C_{1-12}$ aliphatic, aryl, aralkyl, heterocyclyl, or heterocyclylalkyl ring, wherein each of these groups is optionally substituted, and wherein said heterocyclic ring is a three to nine membered saturated or unsaturated mono-, bi-, or tri-heterocyclic ring system wherein each ring contains up to three heteroatoms selected from O, N, or S;

Y is an electronegative leaving group selected from F, Cl, Br, I, arylsulfonyloxy, alkylsulfonyloxy, trifluoromethanesulfonyloxy, OR', SR', —OC=O(R'), or —OPO($R^6$) ($R^7$);
  wherein R' is an aliphatic group, an aryl group, an aralkyl group, a carbocyclic group, an alkyl carbocyclic group, a heterocyclic group, or an alkyl heterocyclic group;
  wherein $R^6$ and $R^7$ are independently selected from R or OR;

$R^2$ is $CO_2H$, $CH_2CO_2H$ or $C_{1-6}$ alkyl esters, $C_{3-10}$ cycloalkyl esters, or cholesterol esters thereof; or primary, secondary or tertiary amides thereof; wherein suitable substituents on the nitrogen of said amides includes one or more $C_{1-6}$ alkyl groups optionally substituted with $N(R)_2$ or 5–6 membered heterocyclic rings containing 1–2 heteroatoms; and
  wherein R is linear or branched $C_{1-12}$ aliphatic;

$R^3$ is selected from H, a side chain of a natural α-amino acid, or a substituted or unsubstituted group having a molecular weight up to about 140 Daltons selected from aliphatic, aryl, aralkyl, heterocyclyl or heterocyclylalkyl ring wherein said heterocyclyl or heterocyclylalkyl ring is a three to nine membered saturated or unsaturated mono-, bi-, or tri-heterocyclic ring system wherein each ring contains up to three heteroatoms selected from O, N, or S; and $R^4$ and $R^5$ taken together with the intervening nitrogen form a mono-, bi- or tricyclic hetero ring system having 1–6 heteroatoms selected from nitrogen, oxygen or sulfur;
  wherein said ring system is optionally substituted with one or more groups independently selected from halogen, —$R^9$, —$OR^9$, —OH, —SH, —$SR^9$, protected OH (such as acyloxy), phenyl (Ph), substituted Ph, —OPh, substituted —OPh, —$NO_2$, —CN, —$NH_2$, —$NHR^9$, —$N(R^9)_2$, —$NHCOR^9$, —NHCONHR$^9$, —NHCON($R^9)_2$, —$NR^9COR^9$, —$NHCO_2R^9$, —$CO_2R^9$, —$CO_2H$, —$COR^9$, —CONHR$^9$, —CON($R^9)_2$, —S(O)$_2R^9$, —$SONH_2$, —S(O)$R^9$, —$SO_2NHR^9$, or —NHS(O)$_2R^9$;
    wherein each $R^9$ is independently selected from an aliphatic group or a substituted aliphatic group;
  wherein the optional substituents on said $C_{1-12}$ aliphatic group or aryl, aralkyl, heterocyclyl, or heterocyclylalkyl ring is independently selected from, from halogen, —$R^{11}$, —$OR^{11}$, —OH, —SH, —$SR^{11}$, acyloxy, substituted or unsubstituted Ph or OPh, —$NO_2$, —CN, —$NH_2$, —$NHR^{11}$, —$N(R^{11})_2$, —$NHCOR^{11}$, —NHCONHR$^{11}$, —NHCON($R^{11})_2$, —$NR^{11}COR^{11}$, —$NHCO_2R^{11}$, —$CO_2R^{11}$, —$CO_2H$, —$COR^{11}$, —CONHR$^{11}$, —CON($R^{11})_2$, —S(O)$_2R^{11}$, —$SONH_2$, —S(O)$R^{11}$, —$SO_2NHR^{11}$, —NHS(O)$_2R^{11}$, =O, =S, =NNHR$^{11}$, =NNR$^{11}$, =N—OR$^{11}$, =NNHCOR$^{11}$, =NNHCO$_2R^{11}$, =NNHSO$_2R^{11}$, or =NR$^{11}$; and
    wherein each $R^{11}$ is independently selected from a $C_{1-12}$ aliphatic group or a substituted $C_{1-12}$ aliphatic group.

2. The compound of claim 1 wherein the compound is selected from those compounds listed in Table 1 below:

| No. | Structure |
|---|---|
| 12 | (structure) |
| 13 | (structure) |
| 14 | (structure) |
| 15 | (structure) |
| 16 | (structure) |

-continued
| No. | Structure |
|---|---|
| 17 | 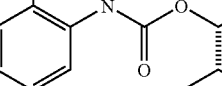 |
| 18 | 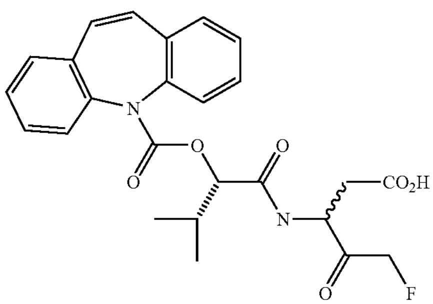 |
| 19 | 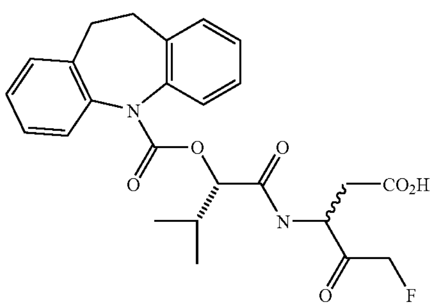 |
| 38 | 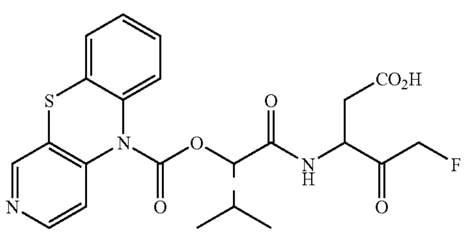 |
| 39 | 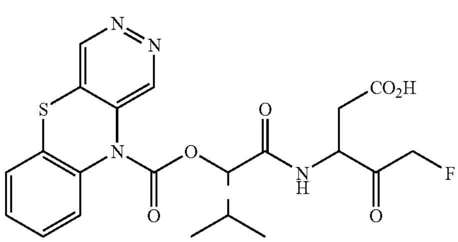 |
| 40 | 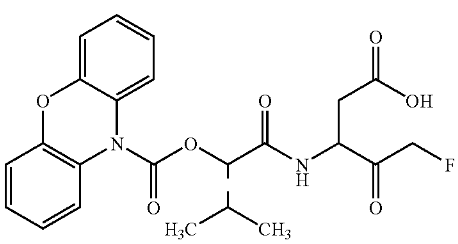 |
-continued
| No. | Structure |
|---|---|
| 41 | 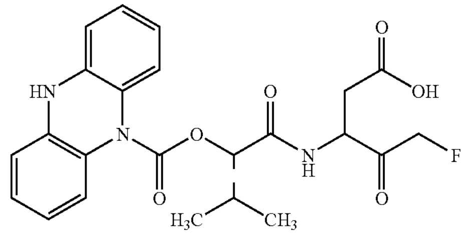 |
| 42 | 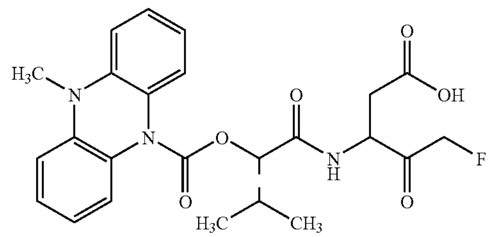 |
| 43 | 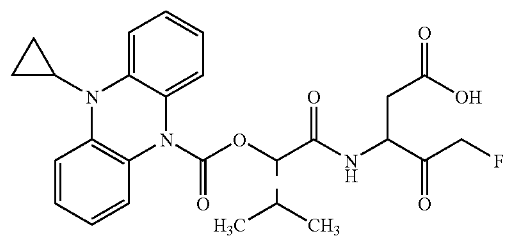 |
| 44 | 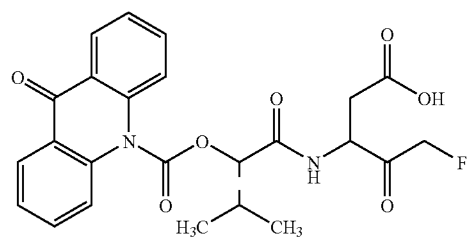 |
| 45 | 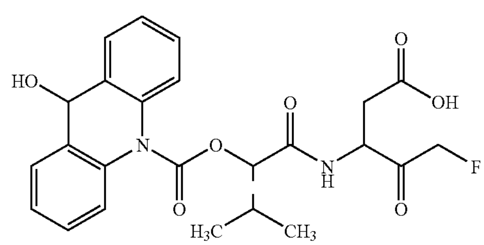 |
| 46 | 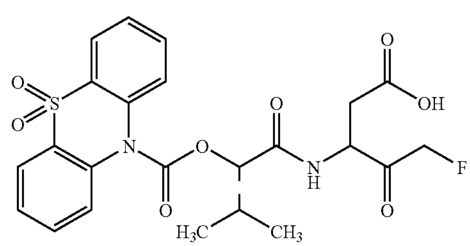 |

-continued

| No. | Structure |
|---|---|
| 47 | 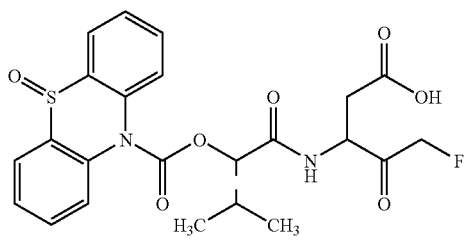 |
| 48 | 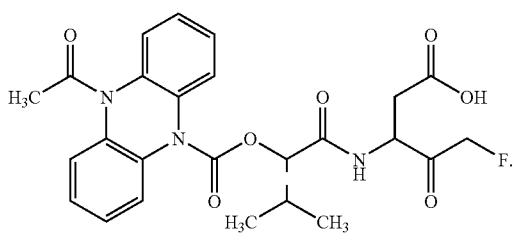 |

3. The compound of claim 1 wherein the compound is selected from the following:

12

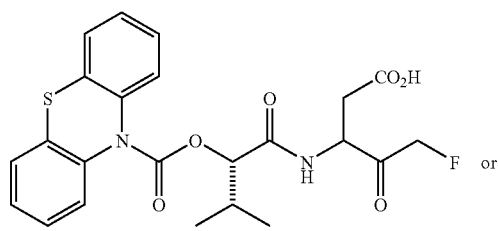

or

17

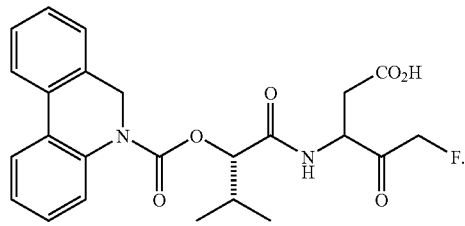

4. The compound according to claim 1 wherein Z is oxygen.

5. The compound according to claim 1 wherein $R^1$ is hydrogen, —R, —CH$_2$OR, —CH$_2$SR, or —CH$_2$Y.

6. The compound according to claim 1 wherein $R^2$ is CO$_2$H, or C$_{1-6}$ alkyl esters, C$_{3-10}$ cycloalkyl esters, or cholesterol esters thereof; or primary, secondary or tertiary amides thereof; wherein suitable substituents on the nitrogen of said amides includes one or more C$_{1-6}$ alkyl groups optionally substituted with N(R)$_2$ or 5–6 membered heterocyclic rings containing 1–2 heteroatoms; and wherein R is linear or branched C$_{1-12}$ aliphatic.

7. The compound according to claim 1 wherein $R^3$ is a group having a molecular weight up to 140 Daltons selected from aliphatic, aryl, aralkyl, heterocyclyl or heterocyclylalkyl ring wherein said heterocyclyl ring is a three to nine membered saturated or unsaturated mono-, bi-, or tri-heterocyclic ring system wherein each ring contains up to three heteroatoms selected from O, N, or S.

8. The compound according to claim 1 wherein $R^4$ and $R^5$ taken together with the intervening nitrogen form a mono-, bi- or tricyclic hetero ring system wherein each ring of the system has 5–7 ring atoms;
wherein said ring system is optionally substituted with one or more groups independently selected from halogen, —$R^9$, —OR$^9$, —OH, —SH, —SR$^9$, protected OH (such as acyloxy), phenyl (Ph), substituted Ph, —OPh, substituted —OPh, —NO$_2$, —CN, —NH$_2$, —NHR$^9$, —N(R$^9$)$_2$, —NHCOR$^9$, —NHCONHR$^9$, —NHCON(R$^9$)$_2$, —NR$^9$COR$^9$, —NHCO$_2$R$^9$, —CO$_2$R$^9$, —CO$_2$H, —COR$^9$, —CONHR$^9$, —CON(R$^9$)$_2$, —S(O)$_2$R$^9$, —SONH$_2$, —S(O)R$^9$, —SO$_2$NHR$^9$, or —NHS(O)$_2$R$^9$; and
wherein each $R^9$ is independently selected from an aliphatic group or a substituted aliphatic group.

9. The compound according to claim 1 wherein Z is oxygen; and
wherein $R^1$ is hydrogen, —R, —CH$_2$OR, —CH$_2$SR, or —CH$_2$Y.

10. The compound according to claim 1 wherein Z is oxygen; and
wherein $R^2$ is CO$_2$H, CH$_2$CO$_2$H or C$_{1-6}$ alkyl esters, C$_{3-10}$ cycloalkyl esters, or cholesterol esters thereof; or primary, secondary or tertiary amides thereof; wherein suitable substituents on the nitrogen of said amides includes one or more C$_{1-6}$ alkyl groups optionally substituted with N(R)$_2$ or 5–6 membered heterocyclic rings containing 1–2 heteroatoms; and wherein R is linear or branched C$_{1-12}$ aliphatic.

11. The compound according to claim 1 wherein Z is oxygen; and
wherein $R^3$ is a group having a molecular weight up to 140 Daltons selected from aliphatic, aryl, aralkyl, heterocyclyl or heterocyclylalkyl ring wherein said heterocyclyl ring is a three to nine membered saturated or unsaturated mono-, bi-, or tri-heterocyclic ring system wherein each ring contains up to three heteroatoms selected from O, N, or S.

12. The compound according to claim 1 wherein Z is oxygen; and
wherein $R^4$ and $R^5$ taken together with the intervening nitrogen form a mono-, bi- or tricyclic hetero ring system wherein each ring of the system has 5–7 ring atoms;
wherein said ring system is optionally substituted with one or more groups independently selected from halogen, —$R^9$, —OR$^9$, —OH, —SH, —SR$^9$, protected OH (such as acyloxy), phenyl (Ph), substituted Ph, —OPh, substituted —OPh, —NO$_2$, —CN, —NH$_2$, —NHR$^9$, —N(R$^9$)$_2$, —NHCOR$^9$, —NHCONHR$^9$, —NHCON(R$^9$)$_2$, —NR$^9$COR$^9$, —NHCO$_2$R$^9$, —CO$_2$R$^9$, —CO$_2$H, —COR$^9$, —CONHR$^9$, —CON(R$^9$)$_2$, —S(O)$_2$R$^9$, —SONH$_2$, —S(O)R$^9$, —SO$_2$NHR$^9$, or —NHS(O)$_2$R$^9$; and
wherein each $R^9$ is independently selected from an aliphatic group or a substituted aliphatic group.

13. The compound according to claim 1 wherein $R^1$ is hydrogen, —R, —CH$_2$OR, —CH$_2$SR, or —CH$_2$Y; and
wherein $R^2$ is CO$_2$H, CH$_2$CO$_2$H or C$_{1-6}$ alkyl esters, C$_{3-10}$ cycloalkyl esters, or cholesterol esters thereof; or primary, secondary or tertiary amides thereof; wherein suitable substituents on the nitrogen of said amides includes one or more C$_{1-6}$ alkyl groups optionally substituted with N(R)$_2$ or 5–6 membered heterocyclic rings containing 1–2 heteroatoms; and wherein R is linear or branched C$_{1-12}$ aliphatic.

14. The compound according to claim 1 wherein $R^1$ is hydrogen, —R, —CH$_2$OR, —CH$_2$SR, or —CH$_2$Y; and wherein $R^3$ is a group having a molecular weight up to 140 Daltons selected from aliphatic, aryl, aralkyl, heterocyclyl or heterocyclylalkyl ring wherein said heterocyclyl ring is a three to nine membered saturated or unsaturated mono-, bi-, or tri-heterocyclic ring system wherein each ring contains up to three heteroatoms selected from O, N, or S.

15. The compound according to claim 1 wherein $R^1$ is hydrogen, —R, —CH$_2$OR, —CH$_2$SR, or —CH$_2$Y; and wherein $R^4$ and $R^5$ taken together with the intervening nitrogen form a mono-, bi- or tricyclic hetero ring system wherein each ring of the system has 5–7 ring atoms;
  wherein said ring system is optionally substituted with one or more groups independently selected from halogen, —R$^9$, —OR$^9$, —OH, —SH, —SR$^9$, protected OH (such as acyloxy), phenyl (Ph), substituted Ph, —OPh, substituted —OPh, —NO$_2$, —CN, —NH$_2$, —NHR$^9$, —N(R$^9$)$_2$, —NHCOR$^9$, —NHCONHR$^9$, —NHCON(R$^9$)$_2$, —NR$^9$COR$^9$, —NHCO$_2$R$^9$, —CO$_2$R$^9$, —CO$_2$H, —COR$^9$, —CONHR$^9$, —CON(R$^9$)$_2$, —S(O)$_2$R$^9$, —SONH$_2$, —S(O)R$^9$, —SO$_2$NHR$^9$, or —NHS(O)$_2$R$^9$; and
  wherein each $R^9$ is independently selected from an aliphatic group or a substituted aliphatic group.

16. The compound according to claim 1 wherein $R^2$ is:
CO$_2$H, CH$_2$CO$_2$H or C$_{1-6}$ alkyl esters, C$_{3-10}$ cycloalkyl esters, or cholesterol esters thereof; or primary, secondary or tertiary amides thereof; wherein suitable substituents on the nitrogen of said amides includes one or more C$_{1-6}$ alkyl groups optionally substituted with N(R)$_2$ or 5–6 membered heterocyclic rings containing 1–2 heteroatoms; and wherein R is linear or branched C$_{1-12}$ aliphatic; and
wherein $R^3$ is a group having a molecular weight up to 140 Daltons selected from aliphatic, aryl, aralkyl, heterocyclyl or heterocyclylalkyl ring wherein said heterocyclyl ring is a three to nine membered saturated or unsaturated mono-, bi-, or tri-heterocyclic ring system wherein each ring contains up to three heteroatoms selected from O, N, or S.

17. The compound according to claim 1 wherein $R^2$ is:
CO$_2$H, CH$_2$CO$_2$H or C$_{1-6}$ alkyl esters, C$_{3-10}$ cycloalkyl esters, or cholesterol esters thereof; or primary, secondary or tertiary amides thereof; wherein suitable substituents on the nitrogen of said amides includes one or more C$_{1-6}$ alkyl groups optionally substituted with N(R)$_2$ or 5–6 membered heterocyclic rings containing 1–2 heteroatoms; and wherein R is linear or branched C$_{1-12}$ aliphatic; and
wherein $R^4$ and $R^5$ taken together with the intervening nitrogen form a mono-, bi- or tricyclic hetero ring system wherein each ring of the system has 5–7 ring atoms;
  wherein said ring system is optionally substituted with one or more groups independently selected from halogen, —R$^9$, —OR$^9$, —OH, —SH, —SR$^9$, protected OH (such as acyloxy), phenyl (Ph), substituted Ph, —OPh, substituted —OPh, —NO$_2$, —CN, —NH$_2$, —NHR$^9$, —N(R$^9$)$_2$, —NHCOR$^9$, —NHCONHR$^9$, —NHCON(R$^9$)$_2$, —NR$^9$COR$^9$, —NHCO$_2$R$^9$, —CO$_2$R$^9$, —CO$_2$H, —COR$^9$, —CONHR$^9$, —CON(R$^9$)$_2$, —S(O)$_2$R$^9$, —SONH$_2$, —S(O)R$^9$, —SO$_2$NHR$^9$, or —NHS(O)$_2$R$^9$; and
  wherein each $R^9$ is independently selected from an aliphatic group or a substituted aliphatic group.

18. The compound according to claim 1 wherein $R^3$ is a group having a molecular weight up to 140 Daltons selected from aliphatic, aryl, aralkyl, heterocyclyl or heterocyclylalkyl ring wherein said heterocyclyl ring is a three to nine membered saturated or unsaturated mono-, bi-, or tri-heterocyclic ring system wherein each ring contains up to three heteroatoms selected from O, N, or S; and
wherein $R^4$ and $R^5$ taken together with the intervening nitrogen form a mono-, bi- or tricyclic hetero ring system wherein each ring of the system has 5–7 ring atoms;
  wherein said ring system is optionally substituted with one or more groups independently selected from halogen, —R$^9$, —OR$^9$, —OH, —SH, —SR$^9$, protected OH (such as acyloxy), phenyl (Ph), substituted Ph, —OPh, substituted —OPh, —NO$_2$, —CN, —NH$_2$, —NHR$^9$, —N(R$^9$)$_2$, —NHCOR$^9$, —NHCONHR$^9$, —NHCON(R$^9$)$_2$, —NR$^9$COR$^9$, —NHCO$_2$R$^9$, —CO$_2$R$^9$, —CO$_2$H, —COR$^9$, —CONHR$^9$, —CON(R$^9$)$_2$, —S(O)$_2$R$^9$, —SONH$_2$, —S(O)R$^9$, —SO$_2$NHR$^9$, or —NHS(O)$_2$R$^9$; and
  wherein each $R^9$ is independently selected from an aliphatic group or a substituted aliphatic group.

19. The compound according to claim 1 wherein Z is oxygen;
wherein $R^1$ is hydrogen, —R, —CH$_2$OR, —CH$_2$SR, or —CH$_2$Y; and
wherein $R^2$ is:
CO$_2$H, CH$_2$CO$_2$H or C$_{1-6}$ alkyl esters, C$_{3-10}$ cycloalkyl esters, or cholesterol esters thereof; or primary, secondary or tertiary amides thereof; wherein suitable substituents on the nitrogen of said amides includes one or more C$_{1-6}$ alkyl groups optionally substituted with N(R)$_2$ or 5–6 membered heterocyclic rings containing 1–2 heteroatoms; and wherein R is linear or branched C$_{1-12}$ aliphatic.

20. The compound according to claim 1 wherein Z is oxygen;
wherein $R^1$ is hydrogen, —R, —CH$_2$OR, —CH$_2$SR, or —CH$_2$Y; and
wherein $R^3$ is a group having a molecular weight up to 140 Daltons selected from aliphatic, aryl, aralkyl, heterocyclyl or heterocyclylalkyl ring wherein said heterocyclyl ring is a three to nine membered saturated or unsaturated mono-, bi-, or tri-heterocyclic ring system wherein each ring contains up to three heteroatoms selected from O, N, or S.

21. The compound according to claim 1 wherein Z is oxygen;
wherein $R^1$ is hydrogen, —R, —CH$_2$OR, —CH$_2$SR, or —CH$_2$Y; and
wherein $R^4$ and $R^5$ taken together with the intervening nitrogen form a mono-, bi- or tricyclic hetero ring system wherein each ring of the system has 5–7 ring atoms;
  wherein said ring system is optionally substituted with one or more groups independently selected from halogen, —R$^9$, —OR$^9$, —OH, —SH, —SR$^9$, protected OH (such as acyloxy), phenyl (Ph), substituted Ph, —OPh, substituted —OPh, —NO$_2$, —CN, —NH$_2$, —NHR$^9$, —N(R$^9$)$_2$, —NHCOR$^9$, —NHCONHR$^9$, —NHCON(R$^9$)$_2$, —NR$^9$COR$^9$, —NHCO$_2$R$^9$, —CO$_2$R$^9$, —CO$_2$H, —COR$^9$, —CONHR$^9$, —CON(R$^9$)$_2$, —S(O)$_2$R$^9$, —SONH$_2$, —S(O)R$^9$, —SO$_2$NHR$^9$, or —NHS(O)$_2$R$^9$; and
  wherein each $R^9$ is independently selected from an aliphatic group or a substituted aliphatic group.

22. The compound according to claim 1 wherein $R^1$ is hydrogen, —R, —CH$_2$OR, —CH$_2$SR, or —CH$_2$Y;

wherein $R^2$ is:

CO$_2$H, CH$_2$CO$_2$H or C$_{1-6}$ alkyl esters, C$_{3-10}$ cycloalkyl esters, or cholesterol esters thereof; or primary, secondary or tertiary amides thereof; wherein suitable substituents on the nitrogen of said amides includes one or more C$_{1-6}$ alkyl groups optionally substituted with N(R)$_2$ or 5–6 membered heterocyclic rings containing 1–2 heteroatoms; and wherein R is linear or branched C$_{1-12}$ aliphatic;

wherein $R^3$ is a group having a molecular weight up to 140 Daltons selected from aliphatic, aryl, aralkyl, heterocyclyl or heterocyclylalkyl ring wherein said heterocyclyl ring is a three to nine membered saturated or unsaturated mono-, bi-, or tri-heterocyclic ring system wherein each ring contains up to three heteroatoms selected from O, N, or S.

23. The compound according to claim 1 wherein $R^1$ is hydrogen, —R, —CH$_2$OR, —CH$_2$SR, or —CH$_2$Y;

wherein $R^2$ is:

CO$_2$H, CH$_2$CO$_2$H or C$_{1-6}$ alkyl esters, C$_{3-10}$ cycloalkyl esters, or cholesterol esters thereof; or primary, secondary or tertiary amides thereof; wherein suitable substituents on the nitrogen of said amides includes one or more C$_{1-6}$ alkyl groups optionally substituted with N(R)$_2$ or 5–6 membered heterocyclic rings containing 1–2 heteroatoms; and wherein R is linear or branched C$_{1-12}$ aliphatic; and wherein $R^4$ and $R^5$ taken together with the intervening nitrogen form a mono-, bi- or tricyclic hetero ring system wherein each ring of the system has 5–7 ring atoms;

wherein said ring system is optionally substituted with one or more groups independently selected from halogen, —R$^9$, —OR$^9$, —OH, —SH, —SR$^9$, protected OH (such as acyloxy), phenyl (Ph), substituted Ph, —OPh, substituted —OPh, —NO$_2$, —CN, —NH$_2$, —NHR$^9$, —N(R$^9$)$_2$, —NHCOR$^9$, —NHCONHR$^9$, —NHCON(R$^9$)$_2$, —NR$^9$COR$^9$, —NHCO$_2$R$^9$, —CO$_2$R$^9$, —CO$_2$H, —COR$^9$, —CONHR$^9$, —CON(R$^9$)$_2$, —S(O)$_2$R$^9$, —SONH$_2$, —S(O)R$^9$, —SO$_2$NHR$^9$, or —NHS(O)$_2$R$^9$; and wherein each $R^9$ is independently selected from an aliphatic group or a substituted aliphatic group.

24. The compound according to claim 1 wherein $R^1$ is hydrogen, —R, —CH$_2$OR, —CH$_2$SR, or —CH$_2$Y;

wherein $R^3$ is a group having a molecular weight up to 140 Daltons selected from aliphatic, aryl, aralkyl, heterocyclyl or heterocyclylalkyl ring wherein said heterocyclyl ring is a three to nine membered saturated or unsaturated mono-, bi-, or tri-heterocyclic ring system wherein each ring contains up to three heteroatoms selected from O, N, or S; and wherein $R^4$ and $R^5$ taken together with the intervening nitrogen form a mono-, bi- or tricyclic hetero ring system wherein each ring of the system has 5–7 ring atoms;

wherein said ring system is optionally substituted with one or more groups independently selected from halogen, —R$^9$, —OR$^9$, —OH, —SH, —SR$^9$, protected OH (such as acyloxy), phenyl (Ph), substituted Ph, —OPh, substituted —OPh, —NO$_2$, —CN, —NH$_2$, —NHR$^9$, —N(R$^9$)$_2$, —NHCOR$^9$, —NHCONHR$^9$, —NHCON(R$^9$)$_2$, —NR$^9$COR$^9$, —NHCO$_2$R$^9$, —CO$_2$R$^9$, —CO$_2$H, —COR$^9$, —CONHR$^9$, —CON(R$^9$)$_2$, —S(O)$_2$R$^9$, —SONH$_2$, —S(O)R$^9$, —SO$_2$NHR$^9$, or —NHS(O)$_2$R$^9$; and wherein each $R^9$ is independently selected from an aliphatic group or a substituted aliphatic group.

25. The compound according to claim 1 wherein $R^2$ is:

CO$_2$H, CH$_2$CO$_2$H or C$_{1-6}$ alkyl esters, C$_{3-10}$ cycloalkyl esters, or cholesterol esters thereof; or primary, secondary or tertiary amides thereof; wherein suitable substituents on the nitrogen of said amides includes one or more C$_{1-6}$ alkyl groups optionally substituted with N(R)$_2$ or 5–6 membered heterocyclic rings containing 1–2 heteroatoms; and wherein R is linear or branched C$_{1-12}$ aliphatic;

wherein $R^3$ is a group having a molecular weight up to 140 Daltons selected from aliphatic, aryl, aralkyl, heterocyclyl or heterocyclylalkyl ring wherein said heterocyclyl ring is a three to nine membered saturated or unsaturated mono-, bi-, or tri-heterocyclic ring system wherein each ring contains up to three heteroatoms selected from O, N, or S; and wherein $R^4$ and $R^5$ taken together with the intervening nitrogen form a mono-, bi- or tricyclic hetero ring system wherein each ring of the system has 5–7 ring atoms;

wherein said ring system is optionally substituted with one or more groups independently selected from halogen, —R$^9$, —OR$^9$, —OH, —SH, —SR$^9$, protected OH (such as acyloxy), phenyl (Ph), substituted Ph, —OPh, substituted —OPh, —NO$_2$, —CN, —NH$_2$, —NHR$^9$, —N(R$^9$)$_2$, —NHCOR$^9$, —NHCONHR$^9$, —NHCON(R$^9$)$_2$, —NR$^9$COR$^9$, —NHCO$_2$R$^9$, —CO$_2$R$^9$, —CO$_2$H, —COR$^9$, —CONHR$^9$, —CON(R$^9$)$_2$, —S(O)$_2$R$^9$, —SONH$_2$, —S(O)R$^9$, —SO$_2$NHR$^9$, or —NHS(O)$_2$R$^9$; and wherein each $R^9$ is independently selected from an aliphatic group or a substituted aliphatic group.

26. The compound according to claim 1 wherein Z is oxygen;

wherein $R^2$ is:

CO$_2$H, CH$_2$CO$_2$H or C$_{1-6}$ alkyl esters, C$_{3-10}$ cycloalkyl esters, or cholesterol esters thereof; or primary, secondary or tertiary amides thereof; wherein suitable substituents on the nitrogen of said amides includes one or more C$_{1-6}$ alkyl groups optionally substituted with N(R)$_2$ or 5–6 membered heterocyclic rings containing 1–2 heteroatoms; and wherein R is linear or branched C$_{1-12}$ aliphatic; and wherein $R^3$ is a group having a molecular weight up to 140 Daltons selected from aliphatic, aryl, aralkyl, heterocyclyl or heterocyclylalkyl ring wherein said heterocyclyl ring is a three to nine membered saturated or unsaturated mono-, bi-, or tri-heterocyclic ring system wherein each ring contains up to three heteroatoms selected from O, N, or S.

27. The compound according to claim 1 wherein Z is oxygen;

wherein $R^2$ is:

CO$_2$H, CH$_2$CO$_2$H or C$_{1-6}$ alkyl esters, C$_{3-10}$ cycloalkyl esters, or cholesterol esters thereof; or primary, secondary or tertiary amides thereof; wherein suitable substituents on the nitrogen of said amides includes one or more C$_{1-6}$ alkyl groups optionally substituted with N(R)$_2$ or 5–6 membered heterocyclic rings containing 1–2 heteroatoms; and wherein R is linear or branched C$_{1-12}$ aliphatic; and wherein $R^4$ and $R^5$ taken together with the intervening nitrogen form a mono-, bi- or tricyclic hetero ring system wherein each ring of the system has 5–7 ring atoms;
  wherein said ring system is optionally substituted with one or more groups independently selected from halogen, $—R^9$, $—OR^9$, $—OH$, $—SH$, $—SR^9$, protected OH (such as acyloxy), phenyl (Ph), substituted Ph, $—OPh$, substituted $—OPh$, $—NO_2$, $—CN$, $—NH_2$, $—NHR^9$, $—N(R^9)_2$, $—NHCOR^9$, $—NHCONHR^9$, $—NHCON(R^9)_2$, $—NR^9COR^9$, $—NHCO_2R^9$, $—CO_2R^9$, $—CO_2H$, $—COR^9$, $—CONHR^9$, $—CON(R^9)_2$, $—S(O)_2R^9$, $—SONH_2$, $—S(O)R^9$, $—SO_2NHR^9$, or $—NHS(O)_2R^9$; and
  wherein each $R^9$ is independently selected from an aliphatic group or a substituted aliphatic group.

28. The compound according to claim 1 wherein Z is oxygen;
  wherein $R^3$ is a group having a molecular weight up to 140 Daltons selected from aliphatic, aryl, aralkyl, heterocyclyl or heterocyclylalkyl ring wherein said heterocyclyl ring is a three to nine membered saturated or unsaturated mono-, bi-, or tri-heterocyclic ring system wherein each ring contains up to three heteroatoms selected from O, N, or S; and
  wherein $R^4$ and $R^5$ taken together with the intervening nitrogen form a mono-, bi- or tricyclic hetero ring system wherein each ring of the system has 5–7 ring atoms;
    wherein said ring system is optionally substituted with one or more groups independently selected from halogen, $—R^9$, $—OR^9$, $—OH$, $—SH$, $—SR^9$, protected OH (such as acyloxy), phenyl (Ph), substituted Ph, $—OPh$, substituted $—OPh$, $—NO_2$, $—CN$, $—NH_2$, $—NHR^9$, $—N(R^9)_2$, $—NHCOR^9$, $—NHCONHR^9$, $—NHCON(R^9)_2$, $—NR^9COR^9$, $—NHCO_2R^9$, $—CO_2R^9$, $—CO_2H$, $—COR^9$, $—CONHR^9$, $—CON(R^9)_2$, $—S(O)_2R^9$, $—SONH_2$, $—S(O)R^9$, $—SO_2NHR^9$, or $—NHS(O)_2R^9$; and
    wherein each $R^9$ is independently selected from an aliphatic group or a substituted aliphatic group.

29. The compound according to claim 1 wherein Z is oxygen;
  wherein $R^1$ is hydrogen, $—R$, $—CH_2OR$, $—CH_2SR$, or $—CH_2Y$; wherein $R^2$ is:
  $CO_2H$, $CH_2CO_2H$ or $C_{1-6}$ alkyl esters, $C_{3-10}$ cycloalkyl esters, or cholesterol esters thereof; or primary, secondary or tertiary amides thereof; wherein suitable substituents on the nitrogen of said amides includes one or more $C_{1-6}$ alkyl groups optionally substituted with $N(R)_2$ or 5–6 membered heterocyclic rings containing 1–2 heteroatoms; and wherein R is linear or branched $C_{1-12}$ aliphatic; and
  wherein $R^3$ is a group having a molecular weight up to 140 Daltons selected from aliphatic, aryl, aralkyl, heterocyclyl or heterocyclylalkyl ring wherein said heterocyclyl ring is a three to nine membered saturated or unsaturated mono-, bi-, or tri-heterocyclic ring system wherein each ring contains up to three heteroatoms selected from O, N, or S.

30. The compound according to claim 1 wherein Z is oxygen;
  wherein $R^1$ is hydrogen, $—R$, $—CH_2OR$, $—CH_2SR$, or $—CH_2Y$; wherein $R^2$ is:
  $CO_2H$, $CH_2CO_2H$ or $C_{1-6}$ alkyl esters, $C_{3-10}$ cycloalkyl esters, or cholesterol esters thereof; or primary, secondary or tertiary amides thereof; wherein suitable substituents on the nitrogen of said amides includes one or more $C_{1-6}$ alkyl groups optionally substituted with $N(R)_2$ or 5–6 membered heterocyclic rings containing 1–2 heteroatoms; and wherein R is linear or branched $C_{1-12}$ aliphatic; and
  wherein $R^4$ and $R^5$ taken together with the intervening nitrogen form a mono-, bi- or tricyclic hetero ring system wherein each ring of the system has 5–7 ring atoms;
    wherein said ring system is optionally substituted with one or more groups independently selected from halogen, $—R^9$, $—OR^9$, $—OH$, $—SH$, $—SR^9$, protected OH (such as acyloxy), phenyl (Ph), substituted Ph, $—OPh$, substituted $—OPh$, $—NO_2$, $—CN$, $—NH_2$, $—NHR^9$, $—N(R^9)_2$, $—NHCOR^9$, $—NHCONHR^9$, $—NHCON(R^9)_2$, $—NR^9COR^9$, $—NHCO_2R^9$, $—CO_2R^9$, $—CO_2H$, $—COR^9$, $—CONHR^9$, $—CON(R^9)_2$, $—S(O)_2R^9$, $—SONH_2$, $—S(O)R^9$, $—SO_2NHR^9$, or $—NHS(O)_2R^9$; and
    wherein each $R^9$ is independently selected from an aliphatic group or a substituted aliphatic group.

31. The compound according to claim 1 wherein Z is oxygen;
  wherein $R^1$ is hydrogen, $—R$, $—CH_2OR$, $—CH_2SR$, or $—CH_2Y$; wherein $R^3$ is a group having a molecular weight up to 140 Daltons selected from aliphatic, aryl, aralkyl, heterocyclyl or heterocyclylalkyl ring wherein said heterocyclyl ring is a three to nine meinbered saturated or unsaturated mono-, bi-, or tri-heterocyclic ring system wherein each ring contains up to three heteroatoms selected from O, N, or S; and
  wherein $R^4$ and $R^5$ taken together with the intervening nitrogen form a mono-, bi- or tricyclic hetero ring system wherein each ring of the system has 5–7 ring atoms;
    wherein said ring system is optionally substituted with one or more groups independently selected from halogen, $—R^9$, $—OR^9$, $—OH$, $—SH$, $—SR^9$, protected OH (such as acyloxy), phenyl (Ph), substituted Ph, $—OPh$, substituted $—OPh$, $—NO_2$, $—CN$, $—NH_2$, $—NHR^9$, $—N(R^9)_2$, $—NHCOR^9$, $—NHCONHR^9$, $—NHCON(R^9)_2$, $—NR^9COR^9$, $—NHCO_2R^9$, $—CO_2R^9$, $—CO_2H$, $—COR^9$, $—CONHR^9$, $—CON(R^9)_2$, $—S(O)^2R^9$, $—SONH_2$, $—S(O)R^9$, $—SO_2NHR^9$, or $—NHS(O)_2R^9$; and
    wherein each $R^9$ is independently selected from an aliphatic group or a substituted aliphatic group.

32. The compound according to claim 1 wherein Z is oxygen;
  wherein $R^2$ is:
  $CO_2H$, $CH_2CO_2H$ or $C_{1-6}$ alkyl esters, $C_{3-10}$ cycloalkyl esters, or cholesterol esters thereof; or primary, secondary or tertiary amides thereof; wherein suitable substituents on the nitrogen of said amides includes one or more $C_{1-6}$ alkyl groups optionally substituted with $N(R)_2$ or 5–6 membered heterocyclic rings containing 1–2 heteroatoms; and wherein R is linear or branched $C_{1-12}$ aliphatic;
  wherein $R^3$ is a group having a molecular weight up to 140 Daltons selected from aliphatic, aryl, aralkyl, heterocyclyl or heterocyclylalkyl ring wherein said heterocyclyl ring is a three to nine membered saturated or unsaturated mono-, bi-, or tri-heterocyclic ring system wherein each ring contains up to three heteroatoms selected from O, N, or S; and wherein $R^4$ and $R^5$ taken together with the intervening nitrogen form a mono-, bi- or tricyclic hetero ring system wherein each ring of the system has 5–7 ring atoms;

wherein said ring system is optionally substituted with one or more groups independently selected from halogen, —$R^9$, —$OR^9$, —OH, —SH, —$SR^9$, protected OH (such as acyloxy), phenyl (Ph), substituted Ph, —OPh, substituted —OPh, —$NO_2$, —CN, —$NH_2$, —$NHR^9$, —$N(R^9)_2$, —$NHCOR^9$, —NHCONHR$^9$, —NHCON(R$^9$)$_2$, —NR$^9$COR$^9$, —NHCO$_2$R$^9$, —CO$_2$R$^9$, —CO$_2$H, —COR$^9$, —CONHR$^9$, —CON(R$^9$)$_2$, —S(O)$_2$R$^9$, —SONH$_2$, —S(O)R$^9$, —SO$_2$NHR$^9$, or —NHS(O)$_2$R$^9$; and wherein each $R^9$ is independently selected from an aliphatic group or a substituted aliphatic group.

33. The compound according to claim 1 wherein $R^1$ is hydrogen, —R, —$CH_2OR$, —$CH_2SR$, or —$CH_2Y$;

wherein $R^2$ is:

$CO_2H$, $CH_2CO_2H$ or $C_{1-6}$ alkyl esters, $C_{3-10}$ cycloalkyl esters, or cholesterol esters thereof; or primary, secondary or tertiary amides thereof; wherein suitable substituents on the nitrogen of said amides includes one or more $C_{1-6}$ alkyl groups optionally substituted with $N(R)_2$ or 5–6 membered heterocyclic rings containing 1–2 heteroatoms; and wherein R is linear or branched $C_{1-12}$ aliphatic;

wherein $R^3$ is a group having a molecular weight up to 140 Daltons selected from aliphatic, aryl, aralkyl, heterocyclyl or heterocyclylalkyl ring wherein said heterocyclyl ring is a three to nine membered saturated or unsaturated mono-, bi-, or tri-heterocyclic ring system wherein each ring contains up to three heteroatoms selected from O, N, or S; and wherein $R^4$ and $R^5$ taken together with the intervening nitrogen form a mono-, bi- or tricyclic hetero ring system wherein each ring of the system has 5–7 ring atoms;

wherein said ring system is optionally substituted with one or more groups independently selected from halogen, —$R^9$, —$OR^9$, —OH, —SH, —$SR^9$, protected OH (such as acyloxy), phenyl (Ph), substituted Ph, —OPh, substituted —OPh, —$NO_2$, —CN, —$NH_2$, —$NHR^9$, —$N(R^9)_2$, —$NHCOR^9$, —NHCONHR$^9$, —NHCON(R$^9$)$_2$, —NR$^9$COR$^9$, —NHCO$_2$R$^9$, —CO$_2$R$^9$, —CO$_2$H, —COR$^9$, —CONHR$^9$, —CON(R$^9$)$_2$, —S(O)$_2$R$^9$, —SONH$_2$, —S(O)R$^9$, —SO$_2$NHR$^9$, or —NHS(O)$_2$R$^9$; and wherein each $R^9$ is independently selected from an aliphatic group or a substituted aliphatic group.

34. The compound according to claim 1 wherein Z is oxygen;

wherein $R^1$ is hydrogen, —R, —$CH_2OR$, —$CH_2SR$, or —$CH_2Y$; wherein $R^2$ is:

$CO_2H$, $CH_2CO_2H$ or $C_{1-6}$ alkyl esters, $C_{3-10}$ cycloalkyl esters, or cholesterol esters thereof; or primary, secondary or tertiary amides thereof; wherein suitable substituents on the nitrogen of said amides includes one or more $C_{1-6}$ alkyl groups optionally substituted with $N(R)_2$ or 5–6 membered heterocyclic rings containing 1–2 heteroatoms; and wherein R is linear or branched $C_{1-12}$ aliphatic;

wherein $R^3$ is a group having a molecular weight up to 140 Daltons selected from aliphatic, aryl, aralkyl, heterocyclyl or heterocyclylalkyl ring wherein said heterocyclyl ring is a three to nine membered saturated or unsaturated mono-, bi-, or tri-heterocyclic ring system wherein each ring contains up to three heteroatoms selected from O, N, or S; and wherein $R^4$ and $R^5$ taken together with the intervening nitrogen form a mono-, bi- or tricyclic hetero ring system wherein each ring of the system has 5–7 ring atoms;

wherein said ring system is optionally substituted with one or more groups independently selected from halogen, —$R^9$, —$OR^9$, —OH, —SH, —$SR^9$, protected OH (such as acyloxy), phenyl (Ph), substituted Ph, —OPh, substituted —OPh, —$NO_2$, —CN, —$NH_2$, —$NHR^9$, —$N(R^9)_2$, —$NHCOR^9$, —NHCONHR$^9$, —NHCON(R$^9$)$_2$, —NR$^9$COR$^9$, —NHCO$_2$R$^9$, —CO$_2$R$^9$, —CO$_2$H, —COR$^9$, —CONHR$^9$, —CON(R$^9$)$_2$, —S(O)$_2$R$^9$, —SONH$_2$, —S(O)R$^9$, —SO$_2$NHR$^9$, or —NHS(O)$_2$R$^9$; and wherein each $R^9$ is independently selected from an aliphatic group or a substituted aliphatic group.

35. The compound according to claim 1 wherein $R^2$ is $CO_2H$.

36. The compound according to claim 1 wherein $R^1$ is —$CH_2OR$, —$CH_2SR$, or —$CH_2Y$.

37. The compound according to claim 36 wherein $R^1$ is —$CH_2Y$.

38. The compound according to claim 36 wherein $R^1$ is —$CH_2F$.

39. The compound according to claim 1 wherein $R^3$ is a $C_{1-4}$ alkyl group.

40. The compound according to claim 1 wherein $R^1$ is —$CH_2F$ and $R^3$ is a $C_{1-4}$ alkyl group.

41. The compound according to claim 1 wherein $R^4$ and $R^5$ taken together with the intervening nitrogen form a ring selected from isoindole, indoline, indazole, purine, dihydropyridine, benzimidazole, imidazole, imidazoline, pyrrole, pyrrolidine, pyrroline, pyrazole, pyrazoline, pyrazolidine, triazole, piperidine, morpholine, thiomorpholine, piperazine, phenothiazine, phenoxazine, dihydrophenazine, dihydrocinnoline, dihydroquinoxaline, tetrahydroquinoline, tetrahydroisoquinoline, dibenzoazepine, dihydrodibenzoazepine, dihydronaphthyridine, tetrahydronaphthyridine, dihydroacridine, β-carboline, pyrido[4,3-b]indole, 2,3,9-triazafluorene, 9-thia-2,10-diazaanthracene, 3,6,9-triazafluorene, thieno[3,2-b]pyrrole, or dihydrophenanthridine;

wherein said ring is optionally substituted with one or more groups independently selected from halogen, —$R^9$, —$OR^9$, —OH, —SH, —$SR^9$, protected OH (such as acyloxy), phenyl (Ph), substituted Ph, —OPh, substituted —OPh, —$NO_2$, —CN, —$NH_2$, —$NHR^9$, —$N(R^9)_2$, —$NHCOR^9$, —$NHCONHR^9$, —NHCON(R$^9$)$_2$, —NR$^9$COR$^9$, —NHCO$_2$R$^9$, —CO$_2$R$^9$, —CO$_2$H, —COR$^9$, —CONHR$^9$, —CON(R$^9$)$_2$, —S(O)$_2$R$^9$, —SONH$_2$, —S(O)R$^9$, —SO$_2$NHR$^9$, or —NHS(O)$_2$R$^9$; and wherein each $R^9$ is independently selected from an aliphatic group or a substituted aliphatic group.

42. The compound according to claim 41 wherein $R^4$ and $R^5$ taken together with the intervening nitrogen form a ring selected from carbazole, phenothiazine, indole, indoline, 5H-dibenzo[b,f]azepine, 10,11-dihydro-5H-dibenzo[b,f]azepine, β-carboline, pyridol[4,3-b]indole, 2,3,9-triazafluorene, 9-thia-2,10-diazaanthracene, 3,6,9-triazafluorene, thieno[3,2-b]pyrrole, or dihydrophenanthridine;

wherein said ring is optionally substituted with one or more groups independently selected from halogen, —$R^9$, —$OR^9$, —OH, —SH, —$SR^9$, protected OH (such as acyloxy), phenyl (Ph), substituted Ph, —OPh, substituted —OPh, —NO$_2$, —CN, —NH$_2$, —NHR$^9$, —N(R$^9$)$_2$, —NHCOR$^9$, —NHCONHR$^9$, —NHCON(R$^9$)$_2$, —NR$^9$COR$^9$, —NHCO$_2$R$^9$, —CO$_2$R$^9$, —CO$_2$H, —COR$^9$, —CONHR$^9$, —CON(R$^9$)$_2$, —S(O)$_2$R$^9$, —SONH$_2$, —S(O)R$^9$, —SO$_2$NHR$^9$, or —NHS(O)$_2$R$^9$; and wherein each R$^9$ is independently selected from an aliphatic group or a substituted aliphatic group.

43. A pharmaceutical composition comprising a compound according to claim 1 and a pharmaceutically acceptable carrier.

44. A method of treating a caspase-mediated disease selected from osteoarthritis, rheumatoid arthritis or psoriasis, in a patient in need thereof, comprising administering to said patient a therapeutically effective amount of a compound according to formula I:

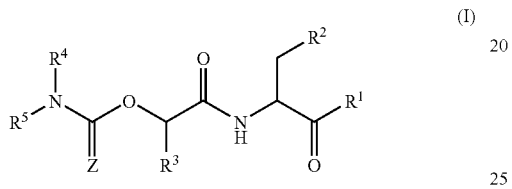

wherein:

Z is oxygen or sulfur;

R$^1$ is hydrogen, —CNN$_2$, —R, —CH$_2$OR, —CH$_2$SR, or —CH$_2$Y;

R is a C$_{1-12}$ aliphatic, aryl, aralkyl, heterocyclyl, or heterocyclylalkyl ring, wherein each of these groups is optionally substituted, and wherein said heterocyclic ring is a three to nine membered saturated or unsaturated mono-, bi-, or tri-heterocyclic ring system wherein each ring contains up to three heteroatoms selected from O, N, or S;

Y is an electronegative leaving group selected from F, Cl, Br, I, arylsulfonyloxy, alkylsulfonyloxy, trifluoromethanesulfonyloxy, OR', SR', —OC═O(R'), or —OPO(R$^6$) (R$^7$);

wherein R'is an aliphatic group, an aryl group, an aralkyl group, a carbocyclic group, an alkyl carbocyclic group, a heterocyclic group, or an alkyl heterocyclic group;

wherein R$^6$ and R$^7$ are independently selected from R or OR;

R$^2$ is CO$_2$H, CH$_2$CO$_2$H or C$_{1-6}$ alkyl esters, C$_{3-10}$ cycloalkyl esters, or cholesterol esters thereof; or primary, secondary or tertiary amides thereof; wherein suitable substituents on the nitrogen of said amides includes one or more C$_{1-6}$ alkyl groups optionally substituted with N(R)$_2$ or 5–6 membered heterocyclic rings containing 1–2 heteroatoms; and wherein R is linear or branched C$_{1-12}$ aliphatic;

R$^3$ is selected from H, a side chain of a natural α-amino acid, or a substituted or unsubstituted group having a molecular weight up to about 140 Daltons selected from aliphatic, aryl, aralkyl, heterocyclyl or heterocyclylalkyl ring wherein said heterocyclyl or heterocyclylalkyl ring is a three to nine membered saturated or unsaturated mono-, bi-, or tri-heterocyclic ring system wherein each ring contains up to three heteroatoms selected from O, N, or S; and R$^4$ and R$^5$ taken together with the intervening nitrogen form a mono-, bi- or tricyclic hetero ring system having 1–6 heteroatoms selected from nitrogen, oxygen or sulfur;

wherein said ring system is optionally substituted with one or more groups independently selected from halogen, —R$^9$, —OR$^9$, —OH, —SH, —SR$^9$, protected OH (such as acyloxy), phenyl (Ph), substituted Ph, —OPh, substituted —OPh, —NO$_2$, —CN, —NH$_2$, —NHR$^9$, —N(R$^9$)$_2$, —NHCOR$^9$, —NHCONHR$^9$, —NHCON(R$^9$)$_2$, —NR$^9$COR$^9$, —NHCO$_2$R$^9$, —CO$_2$R$^9$, —CO$_2$H, —COR$^9$, —CONHR$^9$, —CON(R$^9$)$_2$, —S(O)$_2$R$^9$, —SONH$_2$, —S(O)R$^9$, —SO$_2$NHR$^9$, or —NHS(O)$_2$R$^9$;

wherein each R$^9$ is independently selected from an aliphatic group or a substituted aliphatic group;

wherein the optional substituents on said C$_{1-12}$ aliphatic group or aryl, aralkyl, heterocyclyl, or heterocyclylalkyl ring is independently selected from, from halogen, —R$^{11}$, —OR$^{11}$, —OH, —SH, —SR$^{11}$, acyloxy, substituted or unsubstituted Ph or OPh, —NO$_2$, —CN, —NH$_2$, —NHR$^{11}$, —N(R$^{11}$)$_2$, —NHCOR$^{11}$, —NHCONHR$^{11}$, —NHCON(R$^{11}$)$_2$, —NR$^{11}$COR$^{11}$, —NHCO$_2$R$^{11}$, —CO$_2$R$^{11}$, —CO$_2$H, —COR$^{11}$, —CONHR$^{11}$, —CON(R$^{11}$)$_2$, —S(O)$_2$R$^{11}$, —SONH$_2$, —S(O)R$^{11}$, —SO$_2$NHR$^{11}$, —NHS(O)$_2$R$^{11}$, ═O, ═S, ═NNHR$^{11}$, ═NNR$^{11}$$_2$, ═N—OR$^{11}$, ═NNHCOR$^{11}$, ═NNHCO$_2$R$^{11}$, ═NNHSO$_2$R$^{11}$, or ═NR$^{11}$; and wherein each R$^{11}$ is independently selected from a C$_{1-12}$ aliphatic group or a substituted C$_{1-12}$ aliphatic group.

45. A method for the preservation of cells in an organ for transplant or in a blood product said method comprising the step of bathing the cells in a solution of a compound according to claim 1.

* * * * *